US009796583B2

(12) United States Patent
Coppeta et al.

(10) Patent No.: US 9,796,583 B2
(45) Date of Patent: Oct. 24, 2017

(54) COMPRESSION AND COLD WELD SEALING METHOD FOR AN ELECTRICAL VIA CONNECTION

(75) Inventors: Jonathan R. Coppeta, Windham, NH (US); Kurt Shelton, Woburn, MA (US); Norman F. Sheppard, Jr., New Ipswich, NH (US); Douglas Snell, Amesbury, MA (US); Catherine M. B. Santini, North Chelmsford, MA (US)

(73) Assignee: Microchips Biotech, Inc., Lexington, MA (US)

( * ) Notice: Subject to any disclaimer, the term of this patent is extended or adjusted under 35 U.S.C. 154(b) by 0 days.

(21) Appl. No.: 13/488,355

(22) Filed: Jun. 4, 2012

(65) Prior Publication Data

US 2012/0241216 A1    Sep. 27, 2012

Related U.S. Application Data

(62) Division of application No. 11/267,541, filed on Nov. 4, 2005, now Pat. No. 8,191,756.
(Continued)

(51) Int. Cl.
*B81C 1/00* (2006.01)
*A61K 9/00* (2006.01)
(Continued)

(52) U.S. Cl.
CPC ........ *B81C 1/00269* (2013.01); *A61K 9/0097* (2013.01); *B23K 20/02* (2013.01);
(Continued)

(58) Field of Classification Search
USPC ................................................ 228/115, 116
See application file for complete search history.

(56) References Cited

U.S. PATENT DOCUMENTS 2,983,158 A    5/1961    Hodlewsky et al.
3,024,519 A    3/1962    Scholer et al.
(Continued)

FOREIGN PATENT DOCUMENTS

CN    1529343    9/2004
DE    2331155    1/1974
(Continued)

OTHER PUBLICATIONS

Linnert "Welding Metallurgy" AWS, 1994, 4th ed, p. 616-617.*
(Continued)

*Primary Examiner* — Keith Walker
*Assistant Examiner* — Carlos Gamino
(74) *Attorney, Agent, or Firm* — Eversheds Sutherland (US) LLP

(57) ABSTRACT

Compression cold welding methods, joint structures, and hermetically sealed containment devices are provided. The method includes providing a first substrate having at least one first joint structure which comprises a first joining surface, which surface comprises a first metal; providing a second substrate having at least one second joint structure which comprises a second joining surface, which surface comprises a second metal; and compressing together the at least one first joint structure and the at least one second joint structure to locally deform and shear the joining surfaces at one or more interfaces in an amount effective to form a metal-to-metal bond between the first metal and second metal of the joining surfaces. Overlaps at the joining surfaces are effective to displace surface contaminants and facilitate intimate contact between the joining surfaces without heat input. Hermetically sealed devices can contain drug formulations, biosensors, or MEMS devices.

12 Claims, 26 Drawing Sheets

Related U.S. Application Data

(60) Provisional application No. 60/625,053, filed on Nov. 4, 2004.

(51) Int. Cl.

| | | |
|---|---|---|
| *B23K 20/02* | (2006.01) | |
| *F16B 4/00* | (2006.01) | |
| *F16B 5/08* | (2006.01) | |
| *F16B 11/00* | (2006.01) | |
| *H01L 23/10* | (2006.01) | |
| *H01L 23/31* | (2006.01) | |
| *B33Y 80/00* | (2015.01) | |
| *A61M 5/142* | (2006.01) | |

(52) U.S. Cl.
CPC ...... *B81C 1/00047* (2013.01); *B81C 1/00095* (2013.01); *F16B 4/004* (2013.01); *F16B 5/08* (2013.01); *F16B 11/004* (2013.01); *H01L 23/10* (2013.01); *H01L 23/3142* (2013.01); *A61M 5/14276* (2013.01); *A61M 2205/0244* (2013.01); *A61M 2207/00* (2013.01); *B33Y 80/00* (2014.12); *B81B 2201/06* (2013.01); *B81C 2203/0109* (2013.01); *B81C 2203/019* (2013.01); *B81C 2203/038* (2013.01); *H01L 2224/051* (2013.01); *H01L 2224/05001* (2013.01); *H01L 2224/056* (2013.01); *H01L 2224/05023* (2013.01); *H01L 2224/05568* (2013.01); *H01L 2224/16237* (2013.01); *H01L 2224/81193* (2013.01); *H01L 2924/01322* (2013.01); *H01L 2924/10253* (2013.01); *H01L 2924/1461* (2013.01); *Y10T 403/477* (2015.01)

(56) References Cited

U.S. PATENT DOCUMENTS

| | | | |
|---|---|---|---|
| 3,226,820 | A | 1/1966 | Myron et al. |
| 3,242,555 | A | 3/1966 | Weber et al. |
| 3,735,211 | A | 5/1973 | Kapnias |
| 3,954,122 | A | 5/1976 | Abrahamsen et al. |
| 4,002,284 | A | 1/1977 | Suppus |
| 4,037,749 | A | 7/1977 | Reznicek |
| 4,109,377 | A | 8/1978 | Blazick et al. |
| 4,128,296 | A | 12/1978 | Lauterbach et al. |
| 4,145,627 | A | 3/1979 | Ishizawa |
| 4,804,132 | A | 2/1989 | DiFrancesco |
| 4,865,245 | A | 9/1989 | Schulte et al. |
| 4,935,627 | A | 6/1990 | Zimmermann et al. |
| 4,937,653 | A | 6/1990 | Blonder et al. |
| 5,167,625 | A | 12/1992 | Jacobsen et al. |
| 5,186,379 | A | 2/1993 | Helber, Jr. |
| 5,200,051 | A | 4/1993 | Cozzette et al. |
| RE34,291 | E | 6/1993 | Liguori et al. |
| 5,291,572 | A | 3/1994 | Blonder et al. |
| 5,329,423 | A * | 7/1994 | Scholz .......................... 361/760 |
| 5,366,454 | A | 11/1994 | Currie et al. |
| 5,368,704 | A | 11/1994 | Madou et al. |
| 5,454,506 | A | 10/1995 | Jordhamo et al. |
| RE35,119 | E | 12/1995 | Blonder et al. |
| 5,477,081 | A | 12/1995 | Nagayoshi |
| 5,490,628 | A | 2/1996 | Beatty |
| 5,493,177 | A | 2/1996 | Muller et al. |
| 5,641,713 | A | 6/1997 | Kyle |
| 5,782,891 | A | 7/1998 | Hassler et al. |
| 5,797,898 | A | 8/1998 | Santini, Jr. et al. |
| 5,802,699 | A * | 9/1998 | Fjelstad ............... G01R 1/0466 228/180.22 |
| 5,920,464 | A | 7/1999 | Yokoyama et al. |
| 5,949,187 | A | 9/1999 | Xu et al. |
| 5,956,235 | A | 9/1999 | Kresge et al. |
| 5,974,894 | A | 11/1999 | Delatorre |
| 6,029,881 | A | 2/2000 | Chalco et al. |
| 6,056,734 | A | 5/2000 | Jacobsen et al. |
| 6,060,692 | A | 5/2000 | Bartley et al. |
| 6,062,461 | A | 5/2000 | Sparks et al. |
| 6,070,785 | A | 6/2000 | Ameen et al. |
| 6,114,658 | A | 9/2000 | Roth et al. |
| 6,123,861 | A | 9/2000 | Santini, Jr. et al. |
| 6,221,024 | B1 | 4/2001 | Miesel |
| 6,228,675 | B1 | 5/2001 | Ruby et al. |
| 6,237,389 | B1 | 5/2001 | Tada et al. |
| 6,265,246 | B1 | 7/2001 | Ruby et al. |
| 6,349,232 | B1 | 2/2002 | Gordon |
| 6,376,280 | B1 | 4/2002 | Ruby et al. |
| 6,384,353 | B1 | 5/2002 | Huang et al. |
| 6,392,144 | B1 | 5/2002 | Filter et al. |
| 6,405,592 | B1 | 6/2002 | Murari et al. |
| 6,413,800 | B1 | 7/2002 | Kyle |
| 6,429,511 | B2 | 8/2002 | Ruby et al. |
| 6,436,853 | B2 | 8/2002 | Lin et al. |
| 6,442,307 | B1 | 8/2002 | Carr et al. |
| 6,480,730 | B2 | 11/2002 | Darrow et al. |
| 6,483,030 | B1 | 11/2002 | Glenn et al. |
| 6,491,666 | B1 | 12/2002 | Santini, Jr. et al. |
| 6,499,354 | B1 | 12/2002 | Najafi et al. |
| 6,509,256 | B2 * | 1/2003 | Medlen et al. ............... 438/618 |
| 6,519,075 | B2 | 2/2003 | Carr et al. |
| 6,527,762 | B1 | 3/2003 | Santini, Jr. et al. |
| 6,549,426 | B1 | 4/2003 | Lawlyes et al. |
| 6,551,838 | B2 | 4/2003 | Santini, Jr. et al. |
| 6,627,814 | B1 | 9/2003 | Stark |
| 6,667,544 | B1 | 12/2003 | Glenn |
| 6,669,683 | B2 | 12/2003 | Santini et al. |
| 6,711,317 | B2 | 3/2004 | Jin et al. |
| 6,730,072 | B2 | 5/2004 | Shawgo et al. |
| 6,750,551 | B1 | 6/2004 | Frutschy et al. |
| 6,756,305 | B1 | 6/2004 | Conn |
| 6,767,644 | B2 * | 7/2004 | Aida .......................... 428/473.5 |
| 6,777,263 | B1 | 8/2004 | Gan et al. |
| 6,793,831 | B1 | 9/2004 | Paul et al. |
| 6,808,522 | B2 | 10/2004 | Richards et al. |
| 6,809,412 | B1 | 10/2004 | Tourino et al. |
| 6,822,336 | B2 | 11/2004 | Kurita |
| 6,827,250 | B2 | 12/2004 | Uhland et al. |
| 6,827,584 | B2 | 12/2004 | Mathieu et al. |
| 6,840,427 | B2 | 1/2005 | Ivanov |
| 6,849,463 | B2 | 2/2005 | Santini, Jr. et al. |
| 6,853,067 | B1 | 2/2005 | Cohn et al. |
| 6,872,902 | B2 | 3/2005 | Cohn et al. |
| 6,875,208 | B2 | 4/2005 | Santini, Jr. et al. |
| 6,887,738 | B2 | 5/2005 | Shintani |
| 6,973,718 | B2 | 12/2005 | Sheppard, Jr. et al. |
| 6,976,982 | B2 | 12/2005 | Santini, Jr. et al. |
| 6,998,706 | B2 | 2/2006 | Lawlyes |
| 7,067,397 | B1 | 6/2006 | Chang-Chien et al. |
| 7,112,524 | B2 * | 9/2006 | Hsu et al. ..................... 438/614 |
| 7,129,576 | B2 | 10/2006 | Humpston |
| 7,138,293 | B2 | 11/2006 | Ouellet et al. |
| 7,174,223 | B2 | 2/2007 | Dalton et al. |
| 7,247,933 | B2 | 7/2007 | Juskey et al. |
| 7,341,894 | B2 | 3/2008 | Kimura et al. |
| 7,358,106 | B2 | 4/2008 | Potter |
| 7,443,693 | B2 | 10/2008 | Arnold et al. |
| 7,576,427 | B2 | 8/2009 | Potter |
| 7,651,888 | B2 | 1/2010 | Yang |
| 2002/0017713 | A1 | 2/2002 | Ruby et al. |
| 2002/0054422 | A1 | 5/2002 | Carr et al. |
| 2002/0072784 | A1 | 6/2002 | Sheppard, Jr. et al. |
| 2002/0097952 | A1 | 7/2002 | Jin et al. |
| 2002/0111601 | A1 | 8/2002 | Thompson |
| 2002/0113311 | A1 | 8/2002 | Barchmann et al. |
| 2002/0119176 | A1 | 8/2002 | Greenberg et al. |
| 2002/0144548 | A1 | 10/2002 | Cohn et al. |
| 2002/0179921 | A1 | 12/2002 | Cohn |
| 2002/0187260 | A1 | 12/2002 | Sheppard, Jr. et al. |
| 2003/0010808 | A1 | 1/2003 | Uhland et al. |
| 2003/0189083 | A1 * | 10/2003 | Olsen ............................ 228/115 |
| 2004/0020173 | A1 | 2/2004 | Cho |
| 2004/0028849 | A1 | 2/2004 | Stark et al. |
| 2004/0035698 | A1 | 2/2004 | Ivanov et al. |
| 2004/0067604 | A1 | 4/2004 | Ouellet et al. |
| 2004/0073137 | A1 | 4/2004 | Lloyd et al. |

(56) References Cited

U.S. PATENT DOCUMENTS

| | | |
|---|---|---|
| 2004/0106914 A1 | 6/2004 | Coppeta et al. |
| 2004/0121486 A1 | 6/2004 | Uhland et al. |
| 2005/0005676 A1 | 1/2005 | Crawley et al. |
| 2005/0017329 A1 | 1/2005 | Hayworth et al. |
| 2005/0041366 A1 | 2/2005 | Breven et al. |
| 2005/0050859 A1 | 3/2005 | Coppeta et al. |
| 2005/0055014 A1 | 3/2005 | Coppeta et al. |
| 2005/0077584 A1 | 4/2005 | Polito et al. |
| 2005/0096587 A1 | 5/2005 | Santini, Jr. et al. |
| 2005/0112397 A1 | 5/2005 | Rolfe et al. |
| 2005/0263878 A1 | 12/2005 | Potter |
| 2005/0264979 A1 | 12/2005 | Breyen et al. |
| 2006/0197215 A1 | 9/2006 | Potter |
| 2007/0004079 A1 | 1/2007 | Geefay et al. |
| 2007/0045381 A1 | 3/2007 | Nielsen et al. |
| 2007/0068997 A1 | 3/2007 | Nielsen et al. |
| 2007/0074850 A1 | 4/2007 | Peschl |
| 2007/0159105 A1 | 7/2007 | Bewlay et al. |
| 2007/0161319 A1 | 7/2007 | Bewlay et al. |
| 2008/0026592 A1 | 1/2008 | Shah et al. |
| 2008/0312726 A1 | 12/2008 | Frank et al. |

FOREIGN PATENT DOCUMENTS

| | | | |
|---|---|---|---|
| DE | 19620113 A1 | | 11/1997 |
| DE | 19716683 C1 | | 6/1998 |
| EP | 0347579 A2 | | 12/1989 |
| EP | 0606725 A | | 7/1994 |
| GB | 1568464 | | 5/1980 |
| JP | 61-172362 | | 4/1986 |
| JP | H0513963A A | | 1/1993 |
| JP | 2007134568 A | * | 5/2007 |
| WO | 02056862 A1 | | 7/2002 |
| WO | 2004025727 A | | 3/2004 |

OTHER PUBLICATIONS

Goodman, "Current and Future Uses of Gold in Electronics", Gold Bulletin 2002, p. 21-26.*
Blackstock, et al., "Template Stripping using Cold Welding," J. Vac. Sci. Tehnol., 22(3): 602-605 (2004).
Y.T. Cheng, L. Lin et al., "Localized Silicon Fusion and Eutectic Bonding for MEMS Fabrication and Packaging," Journal of Microelectromechanical Systems 2000, vol. 9, No. 1, pp. 3-8, IEEE Periodicals, New York.
Cohn, et al., "MEMS Packaging on a Budget (Fiscal and Thermal)," The 9th IEEE Int'l Conference on Electronics, Circuits and Systems, 287-290 (Sep. 15-18, 2002).
Eager, "Lecture 4: Cold Welding," MIT (Sep. 13, 2002).
Ferguson, et. al., "Contact Adhesion of Thin Gold Films on Elastomeric Supports: Cold Welding Under Ambient Conditions," Science, New Series, 253(5021): 776-78 (Aug. 16, 1991).
Kim, et. al., "Application of Au—Sn Eutectic Bonding in Hermetic RF MEMS Wafer Level Packaging," 9th Int'l Symposium on Advanced Packaging Materials, 215-219 (Mar. 24-26, 2004).
L. Lin, "MEMS Post-Packaging by Localized Heating and Bonding," IEEE Transactions on Advanced Packaging 2000, vol. 23, No. 4, pp. 608-616, IEEE Periodicals, New York.
Mohamed, et al, "Mechanism of Solid State Pressure Welding," Welding Research Supplement, (Sep. 1975), pp. 302s-310s.
M.B. Cohn, R. Roehnelt et al., (MicroAssembly Technologies, Inc., Richmond, Calif.), "MEMS Packaging on a Budget (Fiscal and Thermal)", IEEE Electronics, Circuits and Systems, 9th Internat'l Conference, vol. 1, pp. 287-290, published on Sep. 15-18, 2002 (incl. 1 pg. Abstract giving pub. date on www.ieee.org visited Jan. 31, 2008).
M.B. Cohn, K. Boehringer et al. "Microassembly Technologies for MEMS", Proceedings Paper (15 pgs.) published Sep. 2, 1998 , Proceedings vol. 3513 pp. 2-16 Microelectronic Structures and MEMS for Optical Processing IV (M. Edward Motamedi, Hans Peter Herzig, Eds.), (available at http://www.ee.washington.edu/research/mems/publications/1998/conferences/spie-mm-cohn-98.pdf) (incl. 1 pg. Abstract from SPIE giving pub. date).
R. Mroczkowski, R. Geckle (AMP, Inc., Harrisburg, Penn.) "Concerning 'Cold Welding' in Crimped Connections", IEEE Electrical Contacts 1995, Proceedings of the 41st Holm Conference, pp. 154-164, pub'd Oct. 2-4, 1995 (incl. 1 pg. Abstract giving pub. date on www.ieee.org visited Jan. 31, 2008).
Niklaus Frank, "Adhesive Wafer Bonding for Microelectronic for Microelectromechanical Systems", Microsystem Technology, Department of Signals, Sensors and Systems, Royal Institute of Technology, ISSN 0281-2878, Stockholm 2002, pp. 1-65.
U.S. Appl. No. 60/574,835, filed May 28, 2004 by Curtis Potter, containing 10 pgs. disclosure (unnumbered) and figs. 1-5, available in US PTO files as related to US Pub. Pat. Appl. 2005/0263878.
U.S. Appl. No. 60/550,844 filed Mar. 8, 2004 by Curtis Potter, containing 10 pgs. disclosure (unnumbered) and figs. 1-5, available in US PTO files as related to US Pub. Pat. Appl. 2006//0197215.
W.Y. Zhang, G.S. Ferguson, S. Tatic-Lucic. "Elastomer-Supported Cold Welding for Room Temperature Wafer-Level Bonding" in Micro Electro Mechanical Systems 2004, 17th IEEE Internat'l Conference pp. 741-744, pub'd. on-line Sep. 27, 2004 (incl. 1 pg. Abstract giving pub. date on www.ieee.org visited Jan. 31, 2008).
W.Y. Zhang, G.S. Ferguson, S. Tatic-Lucic, "Room Temperature Wafer Bonding by Elastomeric Polymer-Supported Cold Welding" in Semiconductor Device Research Symposium, 2003 International, pp. 287-288, pub'd Dec. 10-12, 2003 (incl. 1 pg. Abstract giving pub. date on www.ieee.org visited Jan. 31, 2008).
Takahashi, et al., "Adhesional Bonding of Fine Gold Wires to Metal Substrates," J. Adhesion Sci. Technol., 17 (3):435-51 (2003).
H.-A. Yang, M. Wu et al., "Localized induction heating solder bonding for wafer level MEMS packaging," Journal of Micromechanical Microengineering 2005, vol. 15, pp. 729-732, IOP Publishing, Bristol.
Linnert, Welding Metallurgy, 1994, AWS, 4th ed., pp. 616-617.
IBM Technical Disclosure Bulletin, NN77081012, AGu. 1977.

* cited by examiner

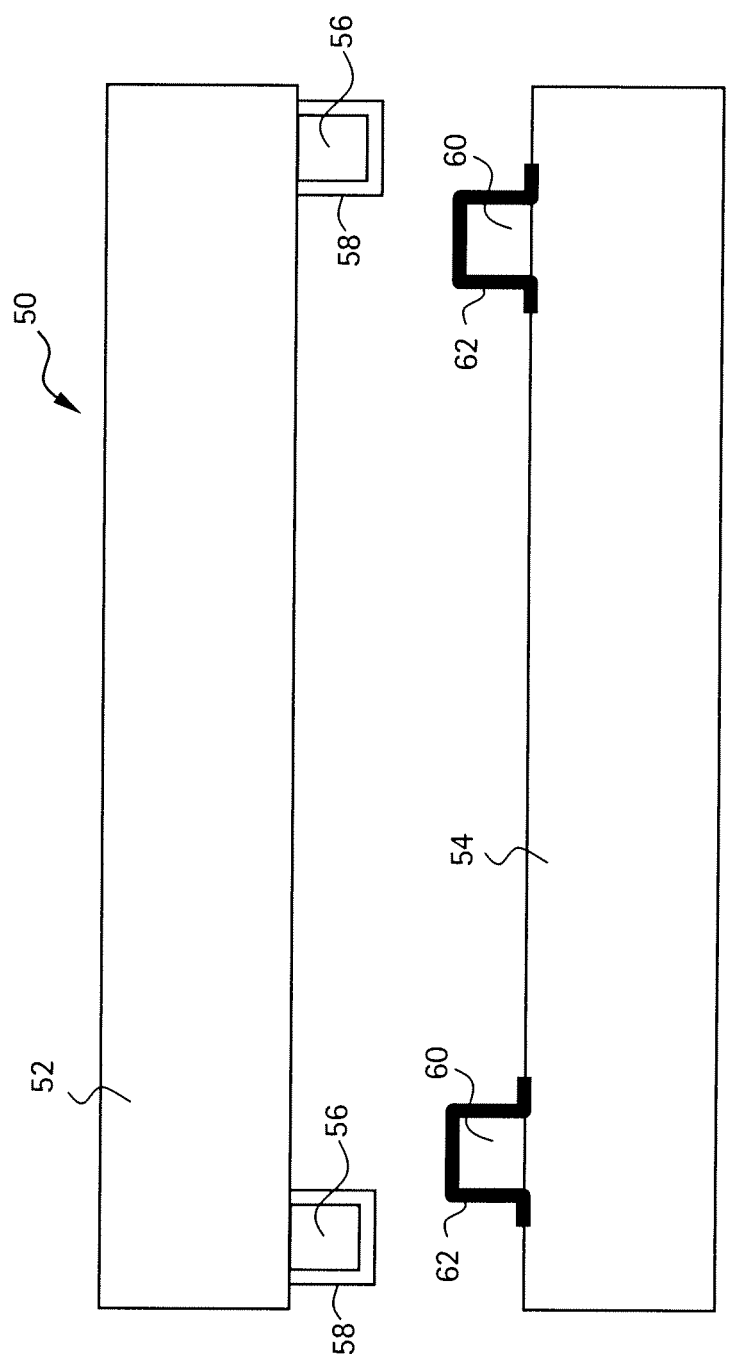

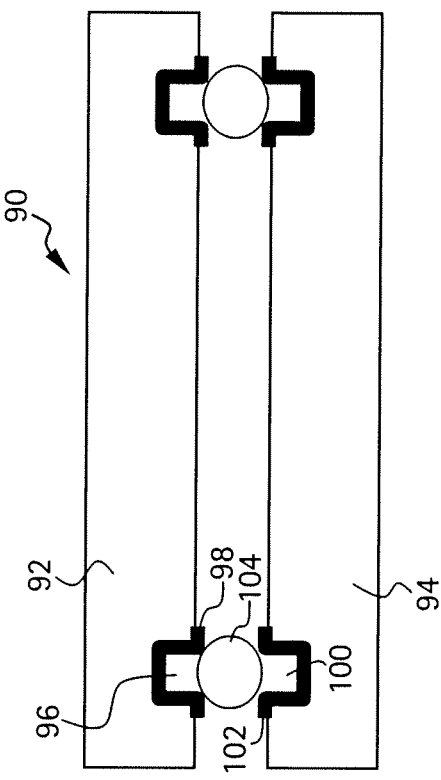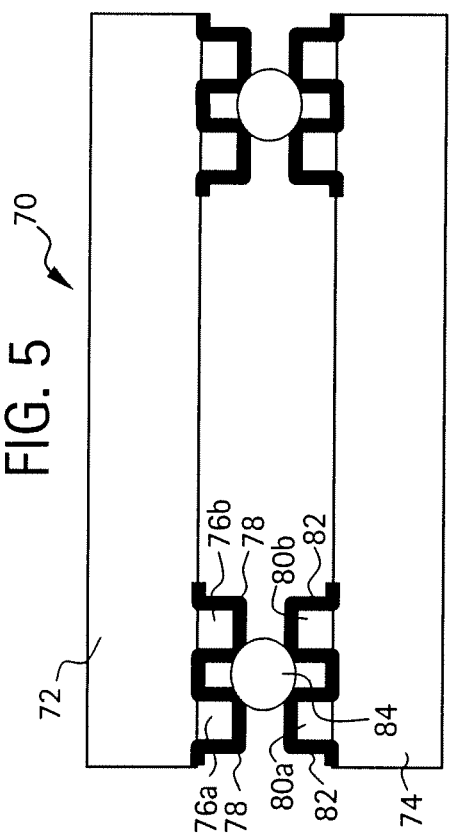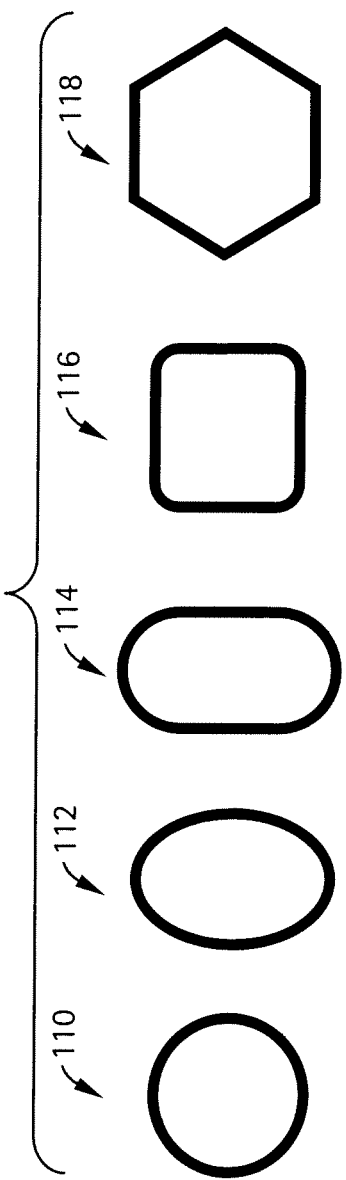

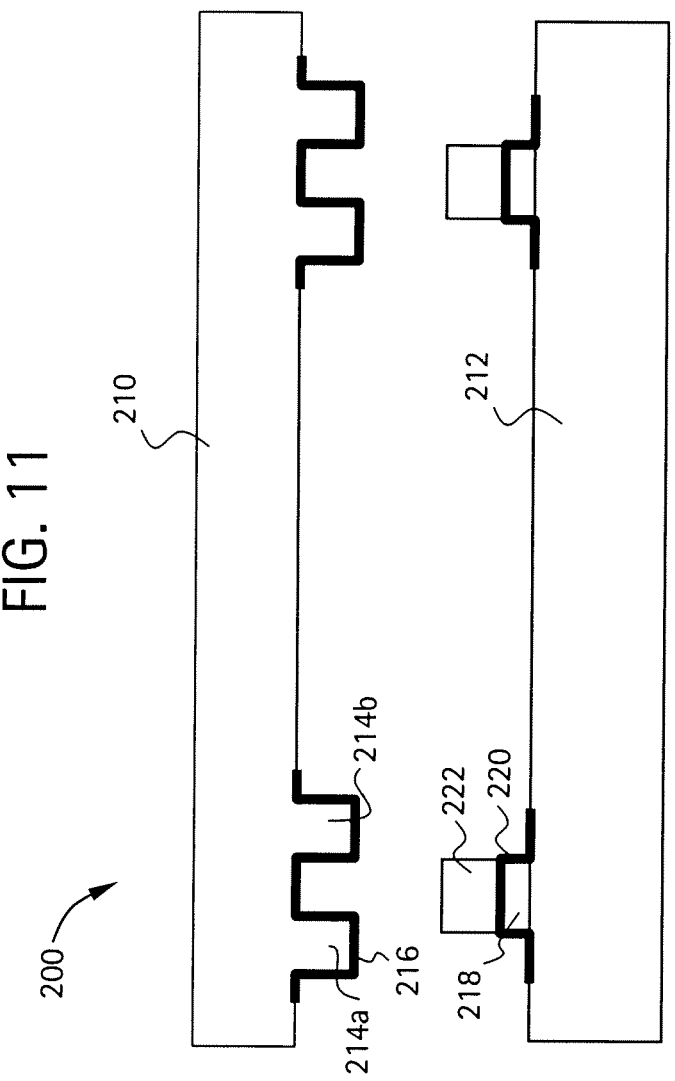

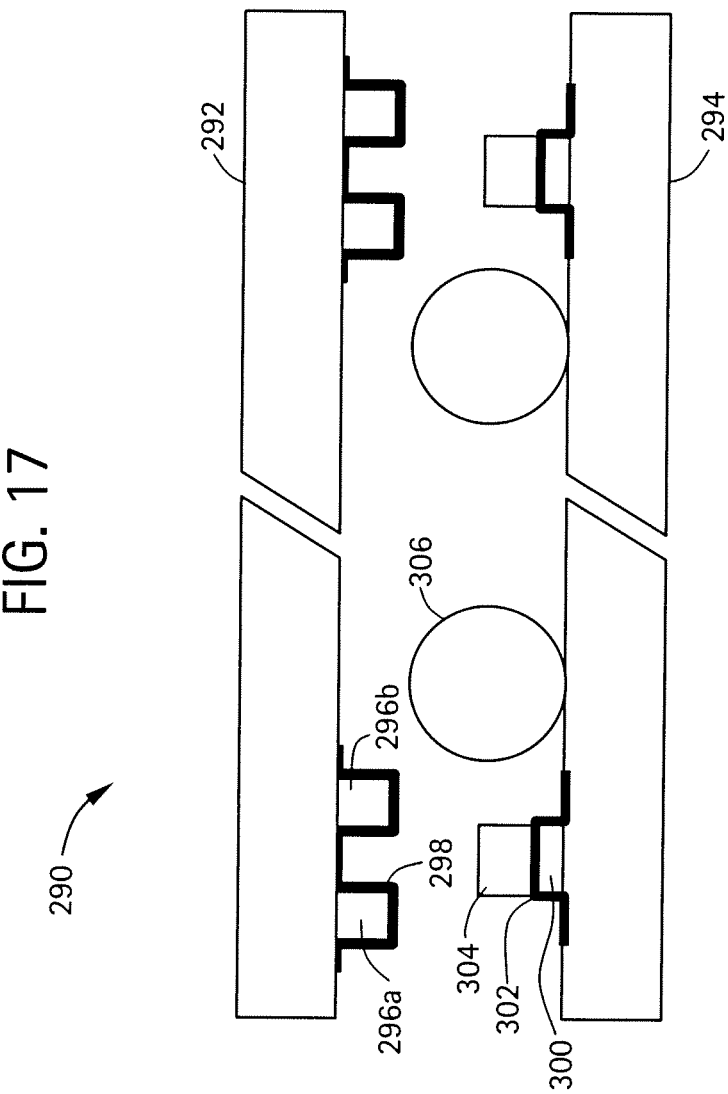

FIG. 21
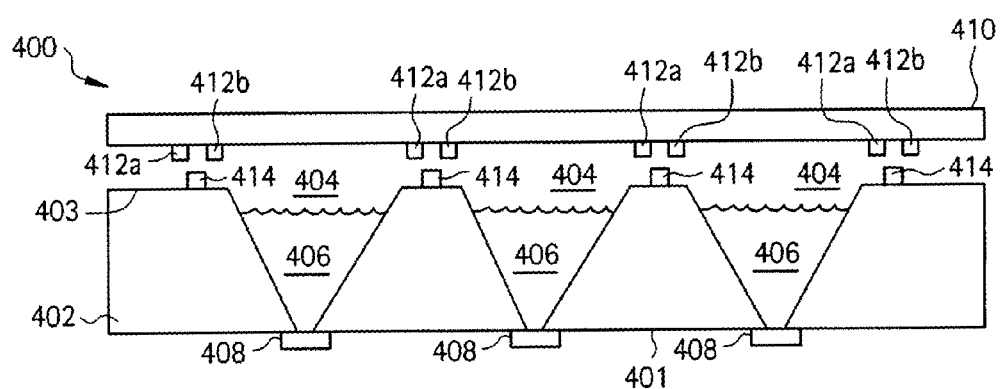
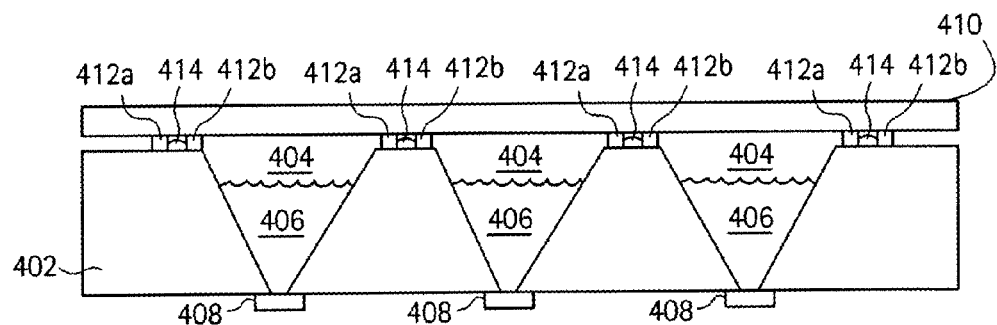

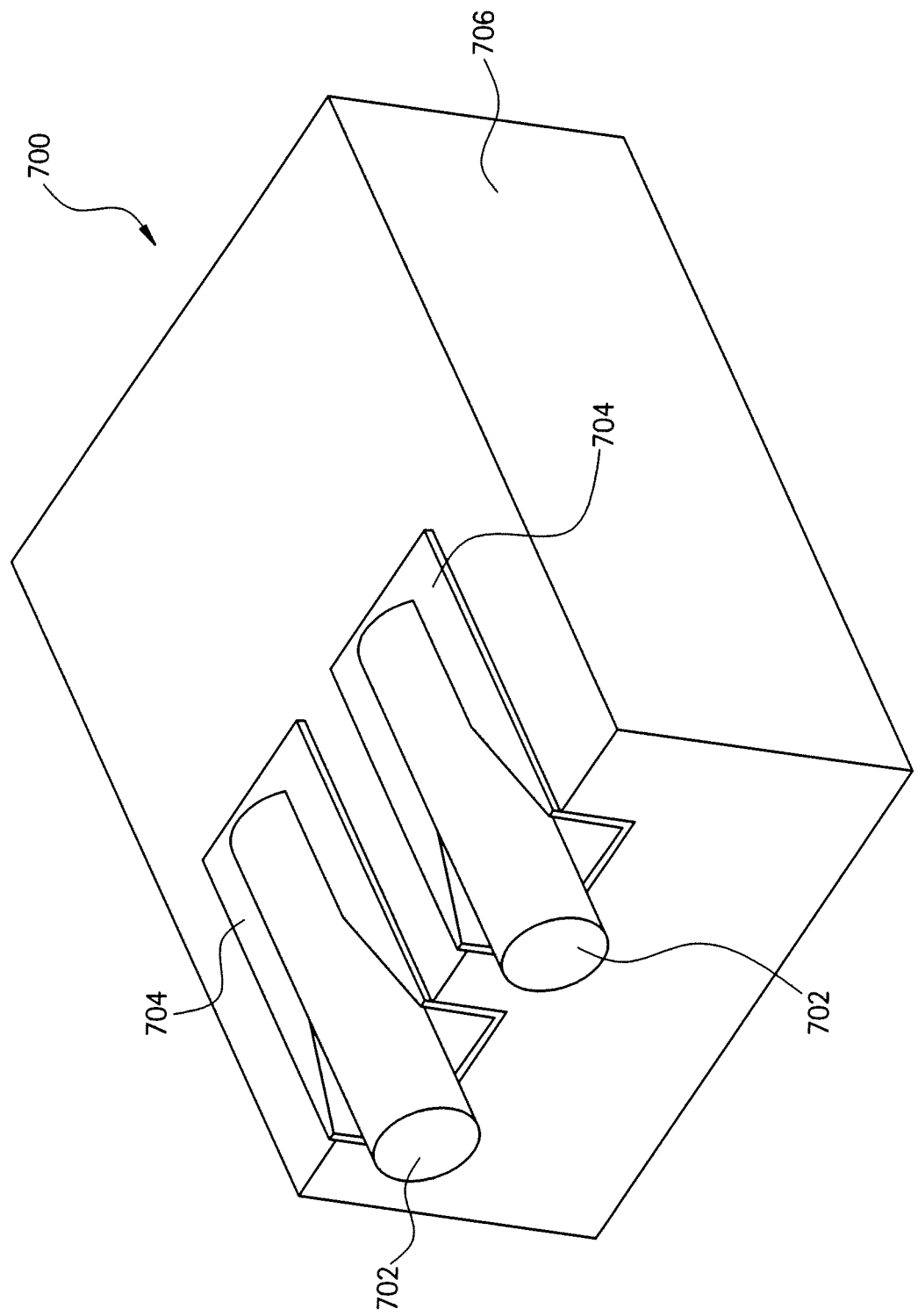

COMPRESSION AND COLD WELD SEALING METHOD FOR AN ELECTRICAL VIA CONNECTION

CROSS-REFERENCE TO RELATED APPLICATIONS

This application is a divisional of U.S. application Ser. No. 11/267,541, filed Nov. 4, 2005, now U.S. Pat. No. 8,191,756, which claims the benefit of U.S. Provisional Application No. 60/625,053, filed Nov. 4, 2004. These applications are incorporated herein by reference in their entirety.

BACKGROUND OF THE INVENTION

This invention is generally in the field of methods and devices for sealing parts together, and more particularly hermetic sealing methods for devices and/or implantable medical devices.

In many applications, there is a need to join, bond, or otherwise seal two or more parts together. Oftentimes, particularly with medical implant devices, these seals must be biocompatible and hermetic, for example, to protect the purity or quality of the reservoir contents.

Examples of devices that may require sealing are described in U.S. Pat. Nos. 5,797,898, 6,527,762, 6,491,666, and 6,551,838, which are incorporated by reference herein. These devices for the controlled release or exposure of reservoir contents include a plurality of reservoirs in which the reservoir contents are contained. The reservoirs may contain pharmaceutical formulations for release, sensors for exposure, or combinations thereof. In constructing these devices, it often is necessary to seal two or more substrates or other parts, which may contain the reservoirs and reservoir contents or electronic components associated with operation of the device.

Various sealing approaches are known in the art. Examples include those described in U.S. Pat. No. 6,730,072 (describing the use of a polymeric gasket and backplate) and U.S. Pat. No. 6,827,250 (describing various techniques for hermetically sealing micro-reservoirs, including high temperature laser or resistive welding, soldering, ultrasonic welding, and metal compression gaskets), and in U.S. Patent Application Publication No. 2005/0050859 A1, which are incorporated by reference herein. These methods may not be suitable or ideal for all sealing applications.

Under ambient conditions, metal surfaces will not typically bond when brought together because the metal surfaces are covered with a surface oxide, an organic contaminant, or both, which act as barriers to metal bond formation. However, the compression of two flat metal surfaces at pressures beyond the yield stress of the metals can cause the surfaces to deform, displacing the barriers and exposing clean metal which can bond. Yet, even with significant metal deformation of two flat surfaces compressed together, the actual bonding area is significantly lower than the mating surfaces area. (Mohamed & Washburn, *Welding Research Supplement*, September 1975, pp. 302s-310s; Welding & Joining Processes 3.371J/13.391J Fabrication Technology, T. Eagar, MIT) This low bonding area characteristic is due to two phenomena. First, the surface fraction of newly exposed metal is not a strong function of the amount of deformation for flat surfaces. Second, asperities prevent the majority of the surface from interacting and bonding. Because the surfaces are not completely bonded, leak paths may be present, preventing a hermetic seal from forming.

Ferguson, et. al., "Contact Adhesion of Thin Gold Films on Elastomeric Supports: Cold Welding Under Ambient Conditions," *Science*, New Series, 253(5021): 776-78 (Aug. 16, 1991) discloses a gold-to-gold bond under ambient conditions by contacting thin gold metal surfaces on top of compliant polymers. However, the result is a bonded interface with "islands" of contaminants that are not bonded. These islands could form a contiguous leak path.

It would be desirable to provide improved sealing methods, for forming hermetic seals at low temperatures with a range of materials. It also would be desirable to individually, hermetically seal a plurality of closely spaced reservoirs between at least two substrates, in a process that is relatively simple and cost effective, particularly for large scale production with high reliability.

SUMMARY OF THE INVENTION

In one aspect, compression cold welding methods and structures are provided for hermetically sealing at least two substrates together. This advantageously can provide a hermetic seal without heat input to the sealing process, which may be desirable in many applications where such additional heat could be detrimental to devices, formulations, or materials in close proximity to the bonding area.

In a preferred embodiment, the method includes providing a first substrate having at least one first joint structure which comprises a first joining surface, which surface comprises a first metal; providing a second substrate having at least one second joint structure which comprises a second joining surface, which surface comprises a second metal; and compressing together the at least one first joint structure and the at least one second joint structure to locally deform and shear the joining surfaces at one or more interfaces in an amount effective to form a metal-to-metal bond between the first metal and second metal of the joining surfaces. In one embodiment, the method further includes aligning the at least one first joint structure above the at least one second joint structure before the compressing step so as to impart one or more overlaps of the at least one first joint structure over the at least on second joint structure, wherein the one or more overlaps create the one or more interfaces of the joining surfaces during the compressing step. In preferred embodiments, the one or more overlaps are effective to displace surface contaminants and facilitate intimate contact between the joining surfaces without heat input. In a particular embodiment, the at least one first joint structure comprises at least one tongue structure and the at least one second joint structure comprises at least one groove structure, and the step of compressing together the at least one first joint structure and the at least one second joint structure includes compressing the at least one tongue structure at least partially into the at least one groove structure. In one embodiment, the at least one tongue structure has a tongue height ranging from 1 micron to 100 microns and a tongue width ranging from 1 micron to 100 microns, and the at least one groove structure has a groove depth ranging from 1 micron to 100 microns and a groove width ranging from 1 micron to 100 microns.

Various combinations of materials of construction may be used. For example, the first metal, the second metal, or both, may comprise gold or platinum. In other embodiments, the first metal, the second metal, or both, comprise a metal selected from the group consisting of gold, indium, aluminum, copper, lead, zinc, nickel, silver, palladium, cadmium, titanium, tungsten, tin, and combinations thereof. The first metal and the second metal may be different metals. The first substrate, the second substrate, or both, may comprise silicon, glasses, ceramics, polymers, metals, and combinations thereof. The first joint structure, the second joint structure, or both, may comprise a material selected from the group consisting of metals, ceramics, glasses, silicon, and combinations thereof. In one embodiment, the first joint structure, the second joint structure, or both, may comprise indium, aluminum, gold, chromium, platinum, copper, nickel, tin, alloys thereof, and combinations thereof.

In one embodiment, the at least one first joint structure is formed by bonding at least one pre-formed structure to the first substrate. The first joining surface may be formed, for example, by an electroplating process, evaporation, a chemical vapor deposition process, sputtering, electron beam evaporation, or a wet etch process. In one embodiment, the first joint structure and first joining surface are a layer of metal covering at least part of a surface of the first substrate.

In one embodiment, the method may further include providing one or more pre-forms between the first substrate and the second substrate, wherein the step of compressing together the at least one first joint structure and the at least one second joint structure further comprises deforming and shearing the one or more pre-forms at pre-form interfaces with the substrates or the joining surfaces. In one embodiment, the pre-forms comprise a metal, a polymer, or a metallized polymer.

In one embodiment, the method further includes heating the joining surfaces at the one or more interfaces. The compressing step and the heating step may occur substantially simultaneously. In one embodiment, the heating of the joining surfaces occurs with a microheater.

In another embodiment, the sealing method further includes applying an ultrasonic energy to the joining surfaces at the one or more interfaces.

In yet other embodiments, the sealing method further includes clamping or soldering together the first substrate and the second substrate.

In a preferred embodiment of the method, the bonded substrates comprise at least one cavity defined therein. In one embodiment, the at least first substrate comprises a plurality of discrete reservoirs containing reservoir contents, each reservoir being hermetically sealed from each other and from an exterior environment. In one example, the reservoir contents comprise a biosensor or other secondary device. In another example, the reservoir contents comprise a drug formulation. In still another example, the reservoir contents comprise fragrance or scent compounds, dyes or other colorants, sweeteners, or flavoring agents. In one embodiment, the first substrate comprises a cavity in which a third substrate is located before the first and second joint structures are compressed together. The third substrate may, for example, comprises a sensor, a MEMS device, or combination thereof.

In one embodiment, the deformation step in the process is conducted under vacuum or in an inert gas atmosphere effective to reduce oxidation of the joint structure relative to that which would occur if conducted in atmospheric air.

In one embodiment, a method is provided for hermetically sealing at least two substrates together, which includes the steps of providing a first substrate having at least one first joint structure which comprises a first joining surface, which surface comprises a first compliant polymer, which has been metallized with a thin layer of a metal; providing a second substrate having at least one second joint structure which comprises a second joining surface, which surface comprises a second compliant polymer, which has been metallized with a thin layer of a metal; and compressing together the at least one first joint structure and the at least one second joint structure to locally deform the joining surfaces at one or more interfaces in an amount effective to form a bond between the first and second the joining surfaces. In one embodiment, the layer of metal of the first or second metallized polymer, or both, comprises gold, platinum or a combination thereof.

In another aspect, a containment device is provided which includes a first substrate having a front side and a back side, and including at least one first joint structure which comprises a first joining surface, which surface is a first metal; a second substrate having at least one second joint structure which comprises a second joining surface, which surface is a second metal; a hermetic seal formed between and joining the first substrate and the second substrate, wherein the hermetic seal is made by compression cold welding the first joining surface to the second joining surface at one or more interfaces; and at least one containment space being defined between the first substrate and the second substrate within the hermetic seal such that the containment space is hermetically sealed an exterior environment. In one embodiment, the at least one containment space comprises a plurality of discrete reservoirs in the at least first substrate positioned between the front side and the back side. In various embodiments, the at least one containment space comprises a sensor, a MEMS device, a drug formulation, or a combination thereof, contained in said containment space. In a preferred embodiment, the joining surfaces are joined together by a metal-to-metal bond formed without heat input. In one embodiment, the at least one first joint structure and the at least one second joint structure comprise a tongue and groove joint.

In various embodiments, the first metal, the second metal, or both, metals may comprise gold, platinum, or a combination thereof, and the substrates may comprise a material selected from the group consisting of silicon, metals, ceramics, polymers, glasses, and combinations thereof. In one embodiment, a pre-form structure is deformed between the first and second joint structures. In another embodiment, the first joint structure or the second joint structure comprises a microheater. Optionally, an intermediate layer may be provided adjacent to the microheater. In one embodiment, the first joint structure or second joint structure may comprise a magnetic material effective to heat the structure via an external induction heater.

The device may further include other securement means, for example, a clamp may be included for joining the substrates together, or a solder material may be used to secure the first substrate and the second substrate together.

In one embodiment, the first substrate further comprises a plurality of discrete openings in communication with the at least one containment space, and said openings are closed by a plurality of discrete reservoir caps. In one embodiment, the reservoir caps comprise a metal film and the device includes means (e.g., control circuitry and power source) for selectively disintegrating the reservoir caps.

In one aspect, an implantable medical device is provided for the controlled exposure or release of contents located in hermetically sealed reservoirs. In one embodiment, the device includes a first substrate; a plurality of discrete reservoirs disposed in the first substrate, the reservoirs having first openings and second openings distal the first openings; reservoir contents located inside the reservoirs, wherein the reservoir contents comprises a drug or a biosensor; a plurality of discrete reservoir caps closing the first openings; means for selectively disintegrating the reservoir caps; and a second substrate and a hermetic joint sealing and closing the second openings, wherein the hermetic joint is made by compression cold-welding. In one embodiment, the hermetic joint comprises a tongue and groove interface.

In another aspect, a method is provided for forming an electrical via connection comprising: providing a first non-conductive substrate having an aperture therethrough, wherein the interior surface of said first substrate defining said aperture comprises a layer of a first electrically conductive material; providing a second non-conductive substrate having a projecting member extending from a surface of said second substrate, wherein said member is formed of or coated with a second electrically conductive material; and compressing the projecting member of said second substrate into the aperture of said first substrate, to locally deform and shear the first and/or second electrically conductive layers, in an amount effective to form a bond and electrical connection between the first and second electrically conductive layers.

BRIEF DESCRIPTION OF THE FIGURES

FIG. 4 is a cross-sectional view of one embodiment of a hermetic seal system having a joint structure design having a single cold welding shear layer at each joint structure.

FIG. 5 is a cross-sectional view of one embodiment of a hermetic seal system having metal pre-forms which can be compression cold welded between joint structures.

FIG. 6 is a cross-sectional view of another embodiment of a hermetic seal system having metal pre-forms which can be compression cold welded between joint structures.

FIG. 7 is plan views of five different embodiments of joint structure base shape geometries.

FIG. 11 is a cross-sectional view of one embodiment of a hermetic seal system having heaters and intermediate layers on the heaters.

FIG. 17 is a cross-sectional view of one embodiment of a hermetic seal system having a cold weld clamp and a compression seal material.

FIG. 21 is a cross-sectional view of an embodiment of a multi-reservoir containment device, illustrating the hermetic sealing of the reservoirs by a compression cold welding process.

FIGS. 24A-B are perspective views of an electrical wire connection made by compression cold welding as described herein. FIG. 24A shows the parts before connection, and FIG. 24B shows the connected assembly.

DETAILED DESCRIPTION OF THE INVENTION

Figure 1:
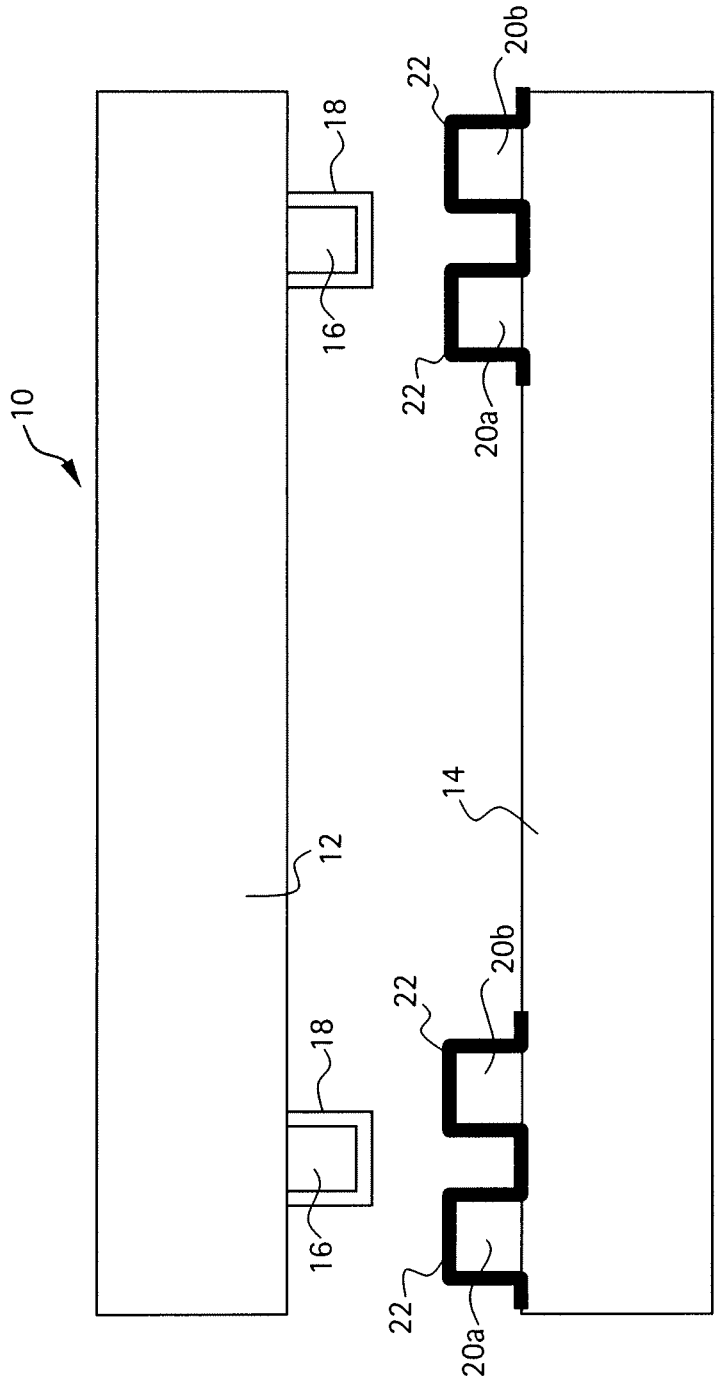
FIG. 1 is a cross-sectional view of one embodiment of a seal system having a tongue and groove joint structure design which provides a hermetic seal formed by a compression cold weld process.

Methods and devices have been developed to form a hermetic seal by a compression cold welding process. The process and seal designs advantageously permit device parts to be bonded together reliably and efficiently, while protecting sensitive device components and contents from heat and solvents. The sealing process involves compression and cold welding together two substrates that are provided with one or more joint sealing surfaces that, during a compression step, locally deform and shear to promote intermolecular diffusion and bonding. Advantageously, the shearing and deformation of metal sealing surfaces substantially scrub away any metal oxides or organic or inorganic contaminants present on the surface, thereby providing an atomically clean metal surface to promote metal-to-metal bonding between the joining surfaces and thus hermeticity. That is, cold welding creates joining surfaces that are free of contaminants and thus free to bond. In a preferred cold welding process, pressures above the yield stress of the metal cause the joining structures and joining surfaces to deform. The metal deformation serves two purposes: It creates intimate contact between the joining surfaces, and it displaces surface oxides and other contaminants so that metal-to-metal bonding can occur. In embodiments where a metal-to-metal bond is formed by cold welding, additional clamps may be unnecessary.

In one aspect, a method is provided for hermetically sealing at least two substrates together, which includes the steps of providing a first substrate having at least one first joint structure which comprises a first joining surface, which surface comprises a first metal; providing a second substrate having at least one second joint structure which comprises a second joining surface, which surface comprises a second metal; compressing together the at least one first joint structure and the at least one second joint structure to locally deform and shear the joining surfaces at one or more interfaces in an amount effective to form a metal-to-metal bond between the first metal and second metal of the joining surfaces. The first metal and second metal may be the same or different. They could be different alloys of the same base metal. If the same metal, the first metal and the second metal may have different structural morphologies, e.g., crystal structures, grain structure, etc. Non-limiting examples of suitable metal surface materials include indium, aluminum, copper, lead, zinc, nickel, silver, palladium, cadmium, titanium, tungsten, tin, and combinations thereof. Gold or platinum may be preferred. The first substrate, the second substrate, or both, may be formed of various materials, such as silicon, glasses, ceramics, polymers, metals, and combinations thereof. Non-limiting examples of substrate materials include quartz, borosilicate glass, aluminum oxide in any of its forms, silicon nitride, and combinations thereof. The substrate and the at least one joint structure may be comprised of the same material or different materials. The joint structure may be formed in/on the substrate by a variety of processes known in the art. Examples include deep reactive ion etching, drilling (e.g., laser), milling, micro-machining, MEMs processing, or LIGA processing of the substrate. The first joint structure, the second joint structure, or both, may comprise a material selected from metals, ceramics, glasses, silicon, and combinations thereof. Examples of possible joint structure materials include the metal surface metals mentioned above, such as indium, aluminum, gold, chromium, platinum, copper, nickel, tin, alloys thereof, and combinations thereof, as well as alumina in any of its forms, quartz, fused silica, silicon oxide, aluminum nitride, silicon carbide, and diamond. The joint structures may be integral with the substrate or bonded to it. In one embodiment, the joint structure is formed by bonding at least one pre-formed structure to its substrate. This pre-formed structure could be formed, for example, by electroplating, chemical vapor deposition, sputtering, MEMS processing, micro-machining, LIGA processing, or anodic bonding. The pre-form structure can be attached to the substrate, for example, by thermocompression, soldering, or ultrasonic welding. The joint structure and its joining surface may be comprised of the same material or different materials.

In one embodiment, the method further includes providing one or more separate pre-forms between the first substrate and the second substrate, wherein the step of compressing together the at least one first joint structure and the at least one second joint structure further comprises deforming and shearing the one or more pre-forms at pre-form interfaces with the substrates or the joining surfaces. The pre-form may be formed, for example, by LIGA processing, MEMS processing, wet etching, laser micro-machining, stamping, cutting, or micro-casting. The pre-forms may comprise a metal, a polymer, or a metallized polymer.

In preferred applications of these methods and seal designs, the hermetic seals are used in sealing microfabricated device components, particularly implantable medical devices. In a preferred embodiment, the present sealing methods and joint structures are used in a device to individually seal an array of containment reservoirs loaded with reservoirs contents, such as drugs for controlled release and/or biosensors, and/or to package associated electronic components for operating the device.

In one aspect, a device is provided that incorporates one or more of these hermetic seals. In one embodiment, the device includes a first substrate (which may include two or more wafers or substrate portions) having a plurality of reservoirs each of which contain a sensor or drug formulation, where each reservoir includes a first opening at a first surface of the device. The first opening is closed by a reservoir cap that can be selectively and actively disintegrated to control the time and/or rate of release or exposure of the reservoir content. In one embodiment the reservoir further includes a second opening distal to the first opening. This opening is hermetically sealed after or simultaneously with loading of the reservoir contents into the reservoir. Typically, this sealing involves bonding the first substrate to a second substrate, using one or more of the hermetic sealing methods and joint designs described herein. Optionally, the device further includes a packaging structure hermetically bonded to a surface of the first or second substrate, to protect electronic components associated with powering and controlling the reservoir cap disintegration and any reservoir based sensors. The packaging structure and hermetic seals protect the electronic components and reservoir contents from the environment. As used herein, the term "environment" refers to the environment external the reservoirs, including biological fluids and tissues at a site of implantation, air, fluids, and particulates present during storage or during in vitro or in vivo use of the device.

As used herein, the term "cold weld" means an intermolecular bond formed without the application of heat, with ambient conditions typically less than 40° C.

As used herein, the term "hermetic seal" refers to preventing undesirable ingress or egress of chemicals into or from one or more compartments of the device, particularly the device reservoirs, over the useful life of the device. For purposes herein, a seal that transmits helium (He) at a rate less than $1\times10^9$ atm*cc/sec is termed hermetic.

As used herein, the terms "comprise," "comprising," "include," and "including" are intended to be open, non-limiting terms, unless the contrary is expressly indicated.

Device Components and Materials

The hermetic seal comprises a first substrate having at least one first joint structure with a first joining surface and a second substrate having at least one second joint structure with a second joining surface, bonded at one or more interfaces by cold welding. In preferred embodiments, the seals are biocompatible and suited for medical implants. In one embodiment, the two substrates may optionally contain one or more of reservoirs, sensors, drugs, and electronics. The substrates may comprise, silicon, glass, Pyrex glass, stainless steel, titanium, alumina, silicon nitride, and other biocompatible ceramics and other metals or polymers. In one embodiment, silicon substrates allow for use of optical probes in the near-infrared (NIR) to infrared (IR) spectrum. It is understood that spectroscopic methods using light in the visible, UV or other wavelengths may be possible by an appropriate selection of substrate material. In addition, the substrate may comprise polymers with high enough Young's Modulus and yield stress to cause high shear during cold welding.

The joint structures (also called "sealing features") on each substrate may comprise the same or a different material than the substrate. For instance, if the joint structures are micro-machined into the substrate, the joint structures are comprised of the substrate material. Alternatively, the joint structures may be a pre-form bonded to the substrate comprised of a different material than the substrate, such as a metal, a metal alloy or a combination of metals. In another embodiment, a LIGA formed nickel joint structure could be electroplated with a layer of gold and then bonded to a metallized substrate using a solder, braze, or thermocompression bond. The LIGA structure could be comprised of any metal or metal alloy compatible with the LIGA process. In yet another embodiment, the joint structure pre-form could be formed from glass or silicon using microelectromechanical system (MEMS) fabrication.

The joint structures have joining surfaces (also called "shear layers" or "bonding surfaces") which are preferably metal and optionally may bond to other joining surfaces. In an alternate embodiment, described in further detail below, the joining surface may be a compliant polymer. Metals with a suitably low plastic deformation stress are used as a joining surface. Suitability can be determined by one skilled in the art, for example, based on the particular joint geometry and the amount of force that can reasonably be applied to form the joint. In addition, metals that do not have a surface oxide or have a high relative oxide to parent metal hardness are preferable for use as a joining surface. See Tylecote, "Investigations on Pressure Welding" *British Welding J.* (March 1954) and Mohamed, et al., "Mechanism of Solid State Pressure Welding" *Welding Research Supplement*, pp. 302-10 (September 1975). Representative examples of suitable metals (and their alloys) include gold (Au), indium (In), aluminum (Al), copper (Cu), lead (Pb), zinc (Zn), nickel (Ni), silver (Ag), platinum (Pt), palladium (Pd), and cadmium (Cd). Representative examples of joining surface metals preferred for biocompatibility include gold and platinum.

The first joining surface may or may not be comprised of the same material as the second joining surface with which the first joining surface will form the hermetic seal. For example, the joining surfaces may be comprised of dissimilar metals or different alloys of the same parent metal. For example, the first joining surface may be gold while the second is platinum. In one embodiment, the joining surfaces are comprised of the same material with a different structural morphology. For instance, a first joining surface may be annealed to reduce the yield stress through the normal annealing mechanisms of recovery, recrystallization, and grain growth, while the second joining surface may be deposited in such a way that the grain size is small, thus increasing the yield stress.

The joining surfaces may comprise the same or a different material than the joint structures. This allows greater freedom in the fabrication method of the joint as well as more design control over the extent and location of plastic deformation. For instance, accurate joint structures can be micro-machined on a silicon substrate and the joint surface material can be deposited on those structures using established MEMs process steps. However, forming accurate joint structures in an alumina substrate may prove difficult and may require alternative materials and fabrication methods. As an example, for alumina substrates, the joint structure may be a deposited metal or alloy with different mechanical properties (e.g., higher elasticity and higher yield stress) than the joining surface. In one embodiment, the joint structure could be an electroplated nickel, an electroplated gold alloy, an electroplated chromium structure, or an electroplated platinum structure. Therefore, it should be understood that a joint structure may need no further processing and have a joining surface comprising the same material as the joint structure, or the joint structure may have at least one other material deposited, electroplated, or formed on the joint structure surface to create a joining surface comprising a different material than the joint structure material. The joint structure may be comprised of a single material or a combination of materials.

Methods of Making a Hermetic Seal

The hermetic seals are made by compression and cold welding. In one embodiment, two substrates are hermetically sealed together by providing a first substrate having at least one first joint structure which comprises a first joining surface which is a metal, providing a second substrate having at least one second joint structure which comprises a second joining surface which is a metal, compressing together at least one first joint structure and at least one second joint structure to locally deform and shear the metal surfaces at one or more interfaces in an amount effective to form a continuous metal-to-metal bond between the joining surfaces at the one or more interfaces.

In some embodiments, ultrasonic energy may be introduced to the hermetic seal joint during the bonding process. While not being bound to any particular mechanism of action, it is believed that the ultrasonic energy may improve the hermetic seal by causing metal-to-metal inter-diffusion by scrubbing the contaminants out of the joining surfaces and deforming the surface asperities so there is intimate contact at the bonding interface.

In other embodiments where the bonding mechanism is not purely cold welding, a pulse of heat or a small increase in temperature may aid in metal bonding by increasing diffusion and lowering the metal's yield stress. For example, induction heating could be used to locally heat the joining surface metals. If other metals are present in the device and are non-magnetic, the joining metals can be selectively heated by incorporating a magnetic material under the joining surfaces. Representative examples of magnetic materials include nickel, iron, cobalt, and combinations thereof. Alternatively, the joint structure geometry may be designed to selectively couple a magnetic field of a given frequency. (See Cao et al., "Selective and localized bonding using induction heating", Solid-State Sensor, Actuator and Microsystems Workshop, Hilton Head Island, S.C., Jun. 2-6, 2002.)

Generally, the ambient environment may be displaced with forming gas, nitrogen, vacuum, or some other condition which would minimize the rate of oxidation and contamination of the joining surfaces as the hermetic bond is formed.

Illustrative Embodiments of the Hermetic Sealing Devices and Systems

Joint structures have been designed to efficiently create large local pressures and deformations at the joining surfaces for a given load. FIGS. 1-6 illustrate cross-sectional views of embodiments of hermetic seal systems having joint structures that efficiently convert a compressive force on the substrates into a shear force on the joining surfaces to cold weld the joint structures together. The shear force is produced by an interference or overlap between the joint structures such that when the joint structures are brought together, there is an overlapping portion of the metal joining surfaces that is deformed by compressive forces. The relative shear of the two overlapping structures eliminates asperities and allows the surfaces to interact and bond. In some embodiments, only the interfering portion of each joint structure will be substantially deformed. In other embodiments, only one joint structure of a pair of joint structures forming a hermetic seal is substantially deformed due to the different materials and associated properties used to form each half of the joint.

The joint structures illustrated in FIGS. 1-6 can be fabricated using conventional MEMs processes, for example, although the structures should also function similarly on a macro-scale. FIGS. 1-6 illustrate only one set of joint structures on each hermetic sealing system, but other embodiments may include multiple sets of joint structures. In addition, the joint structures in FIGS. 1-6 are represented with a rectangular cross-section, but other cross-sections, such as a triangular, rhombus-shaped, or hemispherical joint structure, may also be employed, depending, for example, on the micro-machining limits of geometry definition. For example, a hemispherical joint structure can be created by electroplating a joint structure material onto a photo-lithographically defined seed layer in the absence of a plating mold. In another embodiment, reactive ion etching (RIE) can be used to form a rounded or circular joint structure from a rectangular silicon structure. In yet another embodiment, photoresist can be overexposed and thus undercut during development to form a rhombus-shape which can then be used as a mold for electroplating a joint structure. Multiple layers of photoresist may be used to create more complicated feature geometries.

FIG. 1 illustrates a cross-sectional view of one embodiment of a hermetic seal system 10 having a "tongue and groove" joint structure design which can be sealed by cold welding. The hermetic seal system 10 has a first substrate 12 which has first joint structures 16. The first joint structures each have a first joining surface 18. A second substrate 14 has second joint structures comprising two joint structure elements 20a and 20b. Each second joint structure 20a/20b has a second joining surface 22. The first joint structures 16 create a "tongue" which fits at least partially into a "groove" created by the second joint structures 20a/20b. The width of the tongue as measured across opposite sides of sealing surfaces 18 is greater than the space provided in the groove of the second joint structures joining layer 22. Thus, the first joint structures joining layer 18 and/or the second joint structures joining surface 22 are deformed as the joining structures are compressed together during cold welding, creating shear along the top corners and sidewalls of each joint structure at the joining surfaces 18 and 22.

The first joining surface 18 and the second joining surface 22 may be comprised of the same or different materials. FIG. 1 illustrates one layer of material forming the joining surfaces 18 and 22 and a different material forming the respective joining structures 16 and 20a/20b. In another embodiment, the joining surfaces and/or the joining structure may include multiple layers of materials to fine tune the mechanical or cold weld bonding properties.

Figure 2:
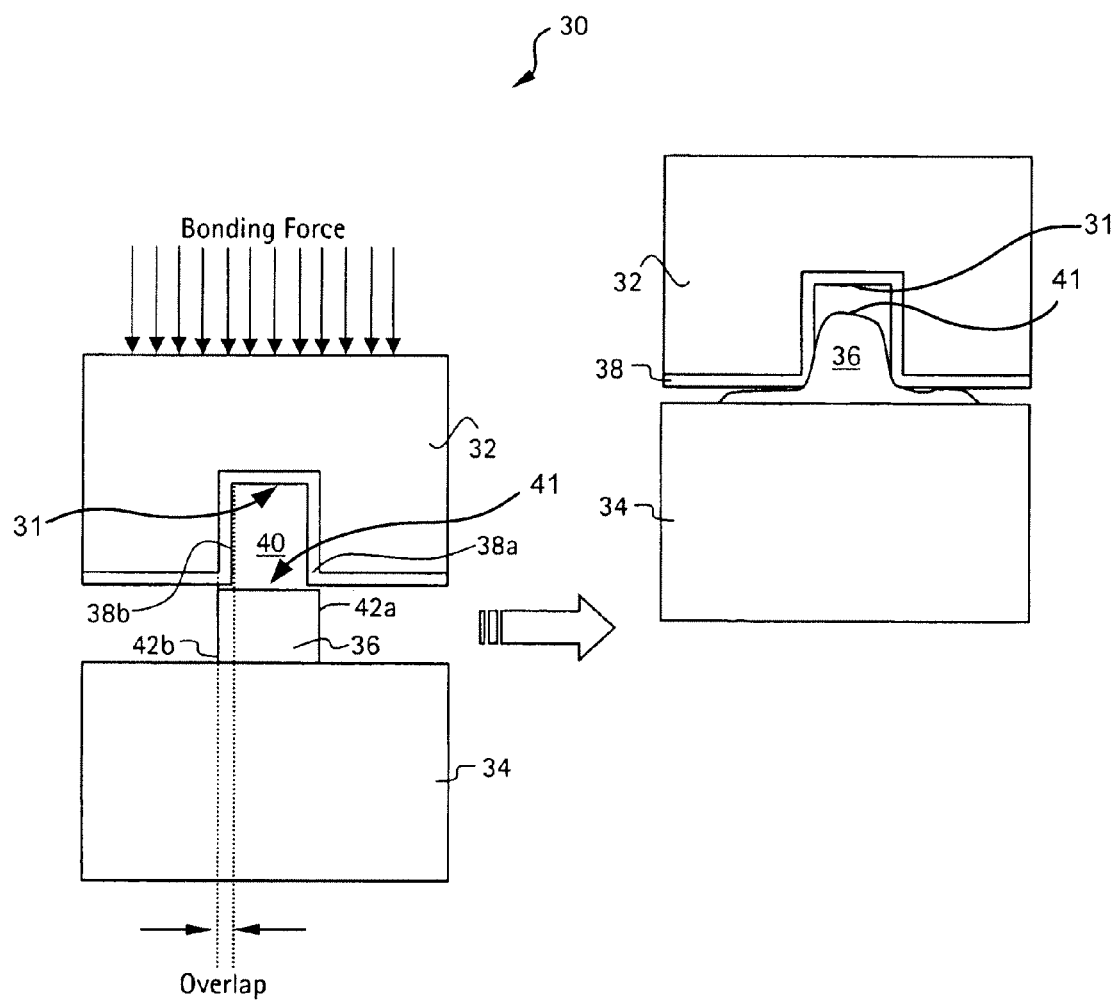
FIG. 2 is a cross-sectional view of another embodiment of a hermetic seal system having a tongue and groove joint structure design, which provides a hermetic seal. The figure on the left shows the structure before the compression cold weld process, and the figure on the right shows the seal formed after the compression cold weld process.

FIG. 2 illustrates a cross-sectional view of another embodiment of a hermetic seal system 30 before and after formation of a hermetic seal using cold welding. The hermetic seal system 30 has a first substrate 32 and a second substrate 34. The first substrate 32 has a first joint structure 40, having a metal joining surface 38a/38b. The first joint structure 40 is in the form of a groove structure formed into the first substrate 32. The second substrate 34 has a second joint structure 36 comprising a different material than the second substrate. The second joint structure 36 has a metal joining surface 42a/42b comprising the same material as the second joint structure. This second joint structure 36 is in the form of a tongue structure, which may partially fit into the groove structure of the first joint structure 40.

A compressive bonding force is applied to the first substrate 32 to cold weld the two substrates together. As the compressive force is applied, the tongue of the second joint structure 36 is deformed into the groove of the first joint structure 40. The deformation arises when the force applied to the area of interference between the first joint structure 40 and the second joint structure 36 results in a pressure exceeding the yield stress of 36. The interference or overlap also creates shear forces at the interface where the joining surfaces 38a/38b, 42a/42b meet. The combination of deformation and shear forces form a metal-to-metal bond between the joining surfaces 38a and 42a and joining surfaces 38b and 42b. Thus, an effective hermetic seal is formed by using cold welding. As shown in the cold welded structure on the right side of FIG. 2, the tip end portion 41 of the tongue structure 36 does not extend into the groove structure 40 enough to contact the inner bottom surface 31 of the groove structure. See, e.g., FIG. 3.

It should be understood that the overlap between the joint structures in FIG. 2 is shown for illustrative purposes and may be smaller or larger than shown. The larger the overlap, the greater the compressive force required to deform the joining layers and thus form a hermetic bond.

In addition, it should be understood that the local deformation at the joining surfaces is a function of the mechanical properties of both the joint structure and the joint surface. For example, in one embodiment, an entire joint structure comprising a solid gold tongue may deform under compression into a silicon groove joint structure. In another embodiment, if the tongue joint structure is silicon and the joining surface is gold, the deformation is localized to the sides and corners of the tongue joint surface.

FIG. 4 illustrates a cross-sectional view of an embodiment of a hermetic seal system 50 having one cold welding shear layer at each joint structure. The hermetic seal system 50 has a first substrate 52 and a second substrate 54. In this embodiment, the first joint surface 58 overlaps with the second joint surface 62 on one side. Having overlap on one side, instead of two sides, of the joint surfaces 58 and 62 may allow a reduction in the overlap required to form a hermetic seal. A reduction in the overlap reduces the compressive force required to form the hermetic seal by cold welding because the yield stress is achieved with a lower force. In an alternate embodiment, the joint structures may be in the form of a triangular or trapezoidal joint structure cross-section to further reduce the shear force required to form the hermetic seal. One disadvantage of this joint design is that only one sealing perimeter can be created, while with a symmetric design (e.g., FIG. 2) there is an opportunity to create two sealing perimeters. A single joint structure such as the tongue and groove combination described herein is generally considered to have two perimeters. Multiple sealing perimeters may advantageously provide a desirable redundancy in a device, providing a "fail-safe" hermetic seal, wherein one or more, but less than all, of the sealing perimeters may be incomplete, or may fail, and the overall seal remains hermetic.

Another embodiment of a hermetic seal system 70 using cold welding is illustrated in FIG. 5. The first substrate 72 and a second substrate 74 are shown before compressive force is applied. The first substrate 72 has first joint structures 76a/76b which have a metal joining surface 78. The first joint structures 76a/76b are aligned with second joint structures 80a/80b, having a metal joining surface 82. Both joint structures 76a/76b and 80a/80b form a groove in which a metal pre-form 84 is entrapped. As the first substrate 72 and the second substrate 74 are compressed together during cold welding, the pre-form 84 is deformed and sheared against the joining surfaces 78 and 82 to form metal-to-metal bonds between the perform and the joining surfaces.

The pre-form 84 may be formed using a LIGA process, wet etch, or laser micro-machining. It should be understood that the processing of the pre-form 84 is dependent upon compatibility of the process with the material used as the pre-form. It should also be understood that the pre-form's cross-sectional geometry may be limited by the fabrication method used. For example, a LIGA technique cannot produce a circular cross-section as illustrated in FIG. 5, but a micro-casting process may enable such a cross-section.

FIG. 6 illustrates a cross-sectional view of another embodiment of a hermetic seal system 90 having a metal pre-form which may be cold welded between two joint structures. The hermetic seal system 90 has a first substrate 92 and a second substrate 94. The first substrate 92 has first joint structures 96 comprising groove structures formed in the first substrate. The first joint structures 96 have a first metal joining surface 98. The second substrate 94 has second joint structures 100 comprising groove structures formed into the substrate and a second metal joining surface 102. Entrapped between the first joint structures 96 and the second joint structures 100 is a metal pre-form 104. The pre-form 104 can be formed using methods similar to the methods described above in reference to the perform 84 in FIG. 5. As the first substrate 92 and the second substrate 94 are compressed together, the pre-form 104 is deformed and sheared against the joining surfaces 98 and 102 to form metal-to-metal bonds between the performs and the joining surfaces to complete the hermetic seal.

Various combinations of preforms, positive features (e.g., a "tongue" or a "tooth") and groove may be used in the compression cold-welding process. In one embodiment, a tongue joint structure on one substrate and a groove joint structure on another substrate having a groove width larger than the width of the tongue joint structure may be cold welded together by compressing a pre-form between them.

The pre-form cross-sectional geometry could be circular, an annulus, a rectangle or other suitable cross-section.

In all of the above embodiments, it may be desirable to minimize the distance between the bonded substrates. This adjustment can be accomplished by minimizing the overlap so that the amount of metal deformed into the space between the substrates is minimized. Additionally, a groove may be created adjacent to a tongue joint structure to provide a volume below the substrate surface for the deformed metal to occupy. Alternatively, the groove structure may have two different widths, a wider opening and a narrower distal end so that metal sheared by the narrower groove flows into the wider groove at the opening.

FIG. 7 illustrates a top view of various embodiments of joint structure base geometries which can be used to form hermetic seals using cold welding. Suitable geometries for the base shape of the joint structure include circle 110, oval 112, hemispheres connected with straight sidewalls 114, square with filleted corners 116, and hexagon 118. Other embodiments of joint structure geometries may include any polygon or an arbitrary path that creates a closed profile. Preferably, sharp corners along the joint structure perimeter are avoided because it may be difficult to form a hermetic seal in such a corner.

Figure 8:
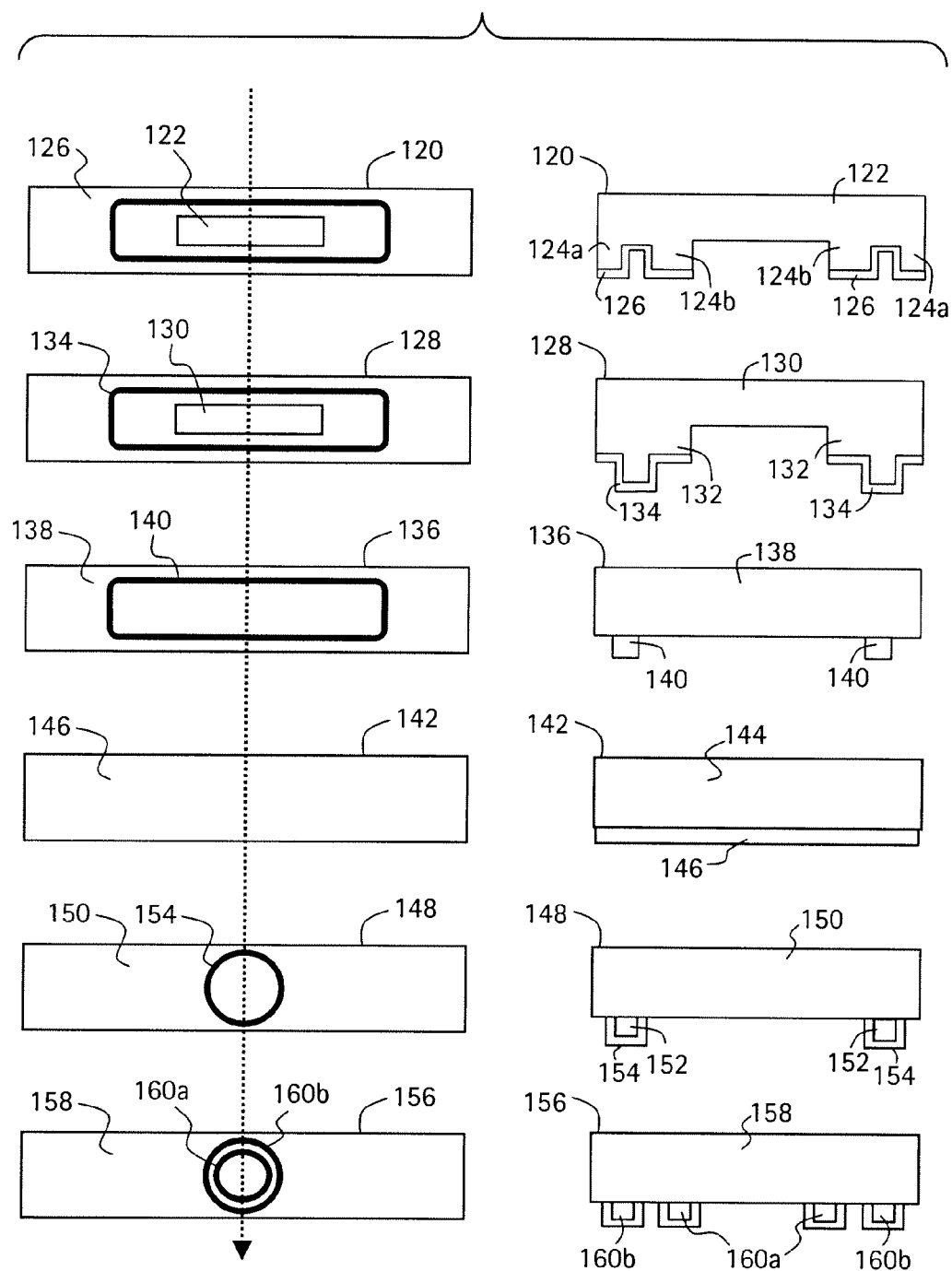
FIG. 8 is plan views and cross-sectional views of six different embodiments of joint structure designs that can be used in compression cold welding to form a hermetic seal.

FIG. 8 illustrates top views and cross-sectional views of various embodiments of joint structure designs that can be fabricated using MEMs processes. These embodiments have only one joint structure set on each substrate, but other embodiments may include an array of circumscribing teeth or grooves serving as multiple joint structure sets. The "tongue" and "groove" geometries are represented in FIG. 8 with a rectangular cross-section, but other cross-sections, such as a triangular or hemispherical geometries, may also be used, depending on the micro-machining limits of cross-section geometry definition. In other embodiments, the substrate may contain an array of reservoirs for drug content or sensors, where each reservoir is required to be hermetically sealed from the other reservoirs and the outside environment.

The joint structures 124a/124b and 132 of joint structure designs 120 and 128 can be fabricated into silicon substrates 122 and 130, respectively, using one and two step deep reactive ion etching (DRIE), respectively, followed by a metal joining surface deposition step. Joint structures 132 and 124a/124b are the MEMs equivalent of a tongue and groove joint, respectively. During cold welding of substrate 122 to substrate 130, the corners of the grooves between joint structures' elements 124a and 124b create high localized stress at the edges of joint structures 132 (the tooth) and the corners of the groove elements 124a and 124b. The high stress causes plastic deformation and shear at the metal interfaces, resulting in intimate contact and bonding between the joining surfaces 126 and 134.

Other embodiments of joint structure designs could be created on a metal substrate by using a combination of milling and plunge electron discharge machining (EDM) steps to create the joint structures and a plating step to metallize the joint structures if necessary.

Joint structure design 136 incorporates tongue joint structures 140 made of a low plastic deformation stress metal, such as indium, aluminum, gold, or copper. Joint structure design 136 has a transparent substrate 138. A Pyrex or similarly transparent substrate, such as sapphire, other glass chemistries, allows the contents of a hermetically sealed device to be optically probed and allows for improved alignment procedures during the cold welding process. The formation of the joint structures 140 from a different material than the substrate 138 obviates the need for creating features in the substrate itself. In addition, joint structure design 136 creates a more deformable joint structure 140 than joint structure design 128 by using a metal with a low plastic deformation stress. Thus, the joint structure 140, with its greater deformation capability, may therefore improve the hermetic seal formed by cold welding.

Joint structure design 142 illustrates a soft deformable metal joining surface 146 to be cold welded to joint structures similar to the joint structures 132, 140, 152, and 160a/160b of joint structure designs 128, 136, 148, and 156, respectively. Joint structure design 142 allows the high local stress from a joint structure protruding from a substrate to cause a groove in the metallized joining surface 146 during cold welding compression. One non-limiting example of a suitable metal for use as the joining surface 146 is gold. The advantage of joint structure design 142 is that alignment issues are greatly reduced. However, joint structure design 142 may be considerably harder to cold weld since the flat joining surface 146 does not efficiently convert the compression force into a shear deformation.

Joint structure design 148 has joint structures 152, which are hybrid joint structures comprised of more than one material, both of which are not the substrate 150 material. Since the joint structures 152 are not formed from the substrate 150 material, modification of deformation characteristics of joint structures 152 can be accomplished without micro-machining the substrate 150. In addition, the joint structures 152 can be comprised of nickel its alloys, or other high Young's Modulus and yield stress material to increase the joint structure's stiffness. The joint structures 152 are subsequently sputter coated with a seed layer for plating joining surfaces 154, which can be indium or gold, for example.

Alternatively, the joint structures 152 could be comprised of a different alloy of the joining surfaces 154 material. In one embodiment, an electroplating deposition process used to deposit the joint structures 152 onto the substrate 150 can also be used to deposit a different alloy as the joining surfaces 154 by changing the plating bath composition during the electroplating process. For example, a hard gold alloy could be plated initially as the joint structures 152, followed by a softer pure gold as the joining surfaces 154.

Joint structure design 156 allows for creation of groove joint structures in conditions where it is not convenient to micro-machine a recessed feature into a substrate 158. A groove is defined by two concentric protruding joint structure elements 160a/160b and can be fabricated using a process similar to the process described above in reference to joint structure design 148 and joint structures 152.

Figure 9:
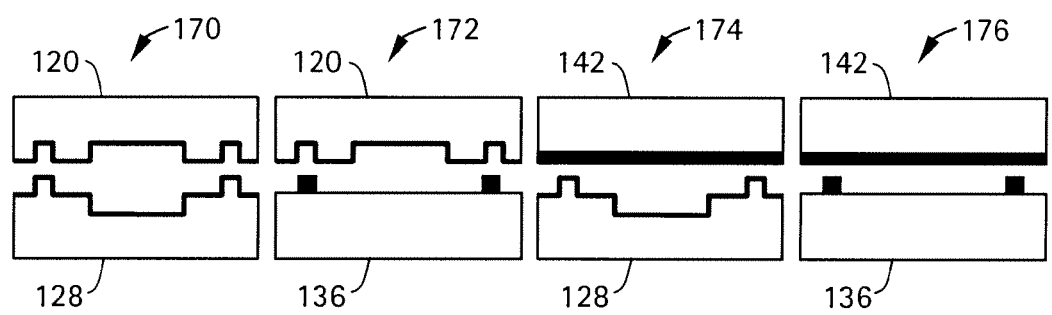
FIG. 9 is cross-sectional views of four embodiments of hermetic seal systems formed with different combinations of the joint structure designs illustrated in FIG. 8.

FIG. 9 illustrates cross-sectional views of various embodiments of the hermetic seal systems comprising various combinations of the joint structure designs illustrated in FIG. 8. Hermetic seal system 170 comprises joint structure design 120 in combination with joint structure design 128. Hermetic seal system 172 comprises joint structure design 120 in combination with joint structure design 136. Hermetic seal system 174 comprises joint structure design 142 in combination with joint structure design 128. Hermetic seal system 176 comprises joint structure design 142 in combination with joint structure design 136.

Dimensions

Figure 10:
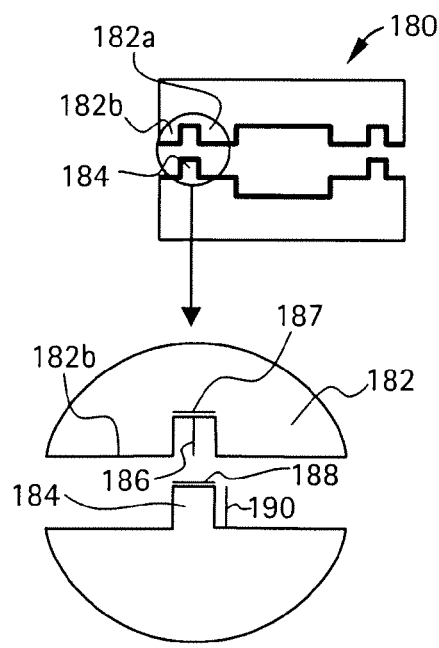
FIG. 10 is a cross-sectional view and a magnified cross-sectional view of an embodiment of a hermetic seal system having a tongue and groove joint structure design.

FIG. 10 illustrates a cross-sectional view and a magnified cross-sectional view of an embodiment of a hermetic seal system 180 having tongue and groove joint structure design. The joint structures 182a/182b and 184 are formed in the silicon substrates by deep reactive ion etching (DRIE). The geometric dimensions of the joint structures 182a/182b, 184 include a groove depth 186, groove width 187, a tongue width 188, and a tongue height 190. Preferably, these geometric dimensions are in the range of about 1 micron to about 100 microns. The tongue and groove joint structures 184 and 182a/182b, respectively, are fabricated to create an overlap (also called an "interference") that exceeds the tolerance in the fabrication of the joint structures and the accuracy tolerance of the assembly equipment to insure that the joint surfaces overlap at all points along the hermetic sealing perimeter. In preferred embodiments, the overlap is in the range of about 1 micron to about 20 microns and is smaller than one quarter of the tongue width 188.

In embodiments wherein the joining surface comprises a different material than the joint structure material and metallization is used to create the joining surfaces, the thicknesses of the metallized joining surfaces are between about 0.1 μm and about 50 μm. Metal thicknesses of about 1 μm can be created by, vapor deposition, for example. Greater metal thicknesses can be created by electroplating processes, for example.

Thermocompression Bonding with Pulsed Heating

In some embodiments of the present invention, selective pulsed heating may be used in thermocompression bonding to form a hermetic seal. The selective pulsed heating may be provided by micro-resistive heaters. Examples of micro-resistive heaters are described in U.S. Pat. No. 6,436,853 to Lin et al. Heaters may be incorporated into any of the embodiments of hermetic sealing systems described herein. Suitable heaters can be placed into one of two groups, heaters with an intermediate layer and heaters without an intermediate layer.

Heaters may require an intermediate layer between the heater and another surface for any combination of the following three reasons: (1) Depending on the electrical resistivity of the materials being used and the amount of heating required, the heater material may need to be electrically insulated from the joining surface and/or the substrate. (2) An intermediate layer may be required in embodiments where the differences in the coefficient of thermal expansion (CTE) between the heater and adjacent materials is large enough to potentially introduce unacceptable stresses at the hermetic seal. During heating, these stresses may manifest themselves by causing delamination, fracturing, or cracking at various interfaces if the stresses exceed the bond strength between the heater and adjacent materials or if the stresses exceed the ultimate tensile strength of any of the materials at the hermetic seal. (3) An intermediate layer may be required as a diffusion barrier to prevent the electrical characteristics of the heater from changing with repeated heating cycles or to slow the diffusion of adhesion layers. Thus, intermediate layers may be required for electrical isolation, for CTE mismatch, for a diffusion barrier, or for any combination of the three depending on the specific materials used.

For simplicity, the intermediate layer between the heater and substrate or any adhesion layers at material interfaces have not been shown in the FIGS. 11-14. Only the intermediate layer between the heater and the joining surface has been shown.

FIG. 11 illustrates a cross-sectional view of one embodiment of a hermetic seal system 200 having heaters 218. The heaters 218 are disposed on a second substrate 212. Intermediate layers 220 are disposed on top of the heaters 218. A joining surface material 222 is heated from below the intermediate layers 220 by the heaters 218. A hermetic seal is formed when the first substrate 210 is joined together with the second substrate 212 and material deformation, in conjunction with pulse heating from the heaters 218, form metal-to-metal bonds between the joining surfaces 216 and the joining surface material 222.

Figure 12:
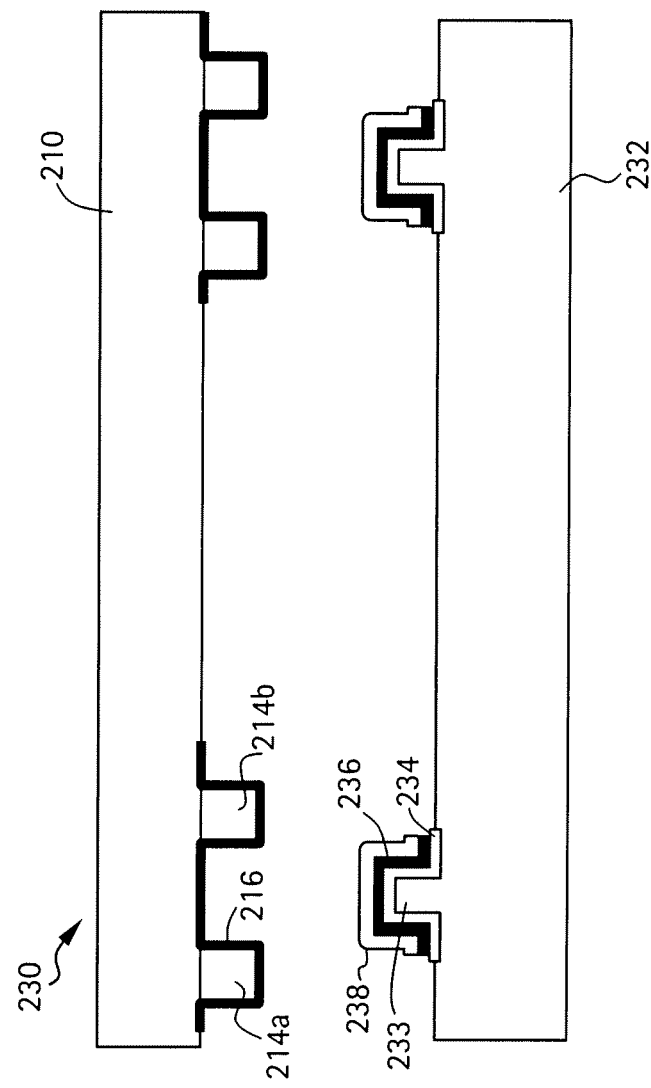
FIG. 12 is a cross-sectional view of one embodiment of a hermetic seal system having microheaters on a joint structure core comprising a substrate material and intermediate layers on the microheaters.

FIG. 12 illustrates another embodiment of a hermetic seal system 230 having heaters 234. In FIG. 12, the second substrate 232 material is the structural core 233 of the joint structures, which comprise structural core 233, the heaters 234, the intermediate layers 236, and the joining surface material 238. In contrast, FIG. 11 illustrates an embodiment in which the heaters 218 and intermediate layers 220 form the core of the joint structure. Thus, the joint structure on second substrate 232 in FIG. 12 can be more rigid than the joint structure on second substrate 212 in FIG. 11. Consequently, more local deformation at the joining surfaces may occur in hermetic seal system 230 during thermocompression bonding. It should be understood that this increased rigidness in the joint structures is also dependant upon the specific materials selected.

Figure 13:
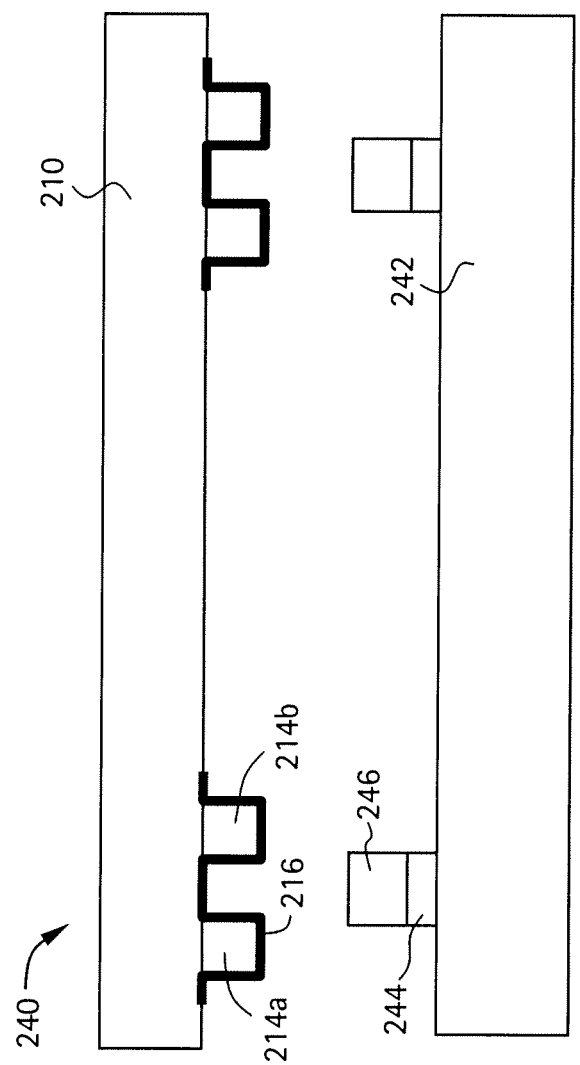
FIG. 13 is a cross-sectional view of one embodiment of a hermetic seal system having microheaters in direct contact with a joining surface material.
Figure 14:
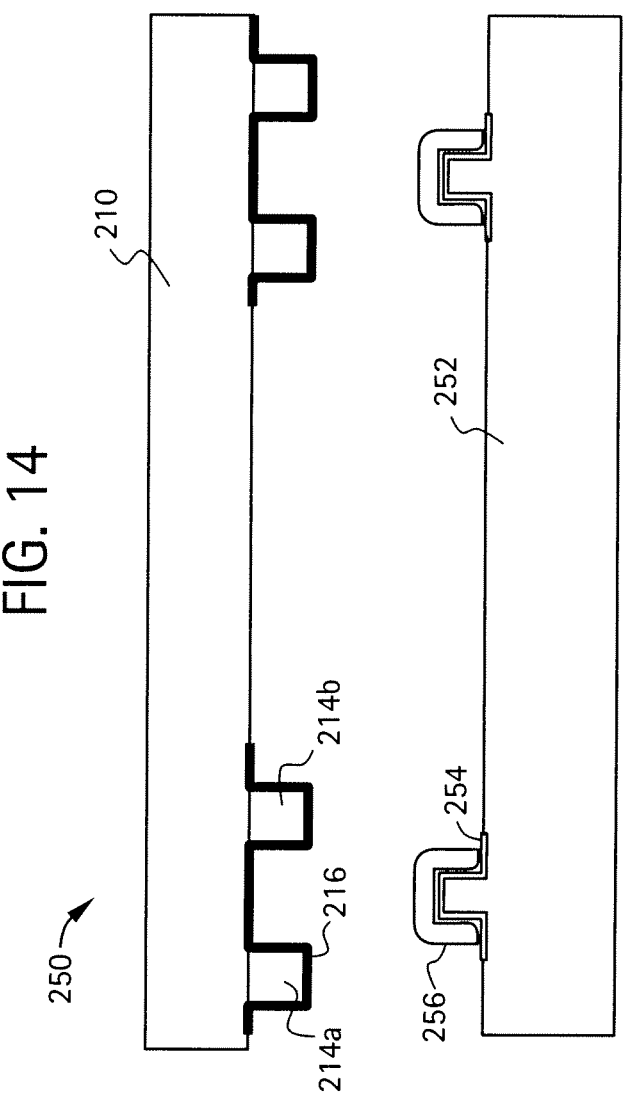
FIG. 14 is a cross-sectional view of one embodiment of a hermetic seal system having microheaters on a joint structure core comprising a substrate material and in direct contact with a joining surface material.

FIG. 13 illustrates an embodiment of a hermetic seal system 240 having heaters 244 in contact with the joining surface material 246. FIG. 14 illustrates another embodiment of a hermetic seal system 250 having heaters 254 in contact with the joining surface material 256. In FIG. 14, the joint structure cores on the second substrate 252 comprise substrate material and may be a stiffer joint structure than the joint structures on the second substrate 242 in FIG. 13, which do not comprise substrate material. The joining surface materials 246 and 256 may be heated primarily from the heaters 244 and 254 underneath. In an alternate embodiment, the joining surface material may be heated directly by passing a current through the joining surface.

It should be understood that the embodiments illustrated in FIGS. 11-14 may have a first substrate and second substrate comprising different materials. In addition, the joint structures of the first substrate may comprise the same material or a different material than the joining surfaces of the first substrates and the joining surfaces of the second substrates. Furthermore, the joining surfaces on the first substrates and the joining surfaces on the second substrates may comprise the same material or different materials. The joining surfaces of the second substrates and the heaters may comprise the same material or different materials. In addition, the bonding surface may melt during the pulsed heating, as would be the case in soldering processes.

Minimization of the Mechanical Force Required for Cold Welding

Minimization of the mechanical force required to bond the substrates can reduce the risk of damaging the substrate or substrate coatings. Minimizing the mechanical force required can be accomplished by various methods. These methods include various joint structure designs, joining surface material selections, joining surface material processing procedures, and cold welding process parameters.

For example, the total amount of interference or overlap between the sealing features is governed by the joint structure design. A greater overlap or interference between mating joint structures requires a larger force to cold weld, since a larger volume of metal is being deformed during the cold welding process. Therefore, to minimize the force required, the total amount of metal deformed should be minimized. This can be accomplished by minimizing the shear layer or interface of the joining surface and also minimizing the amount of interference between joint structures. Preferably, the overlap would be just slightly larger than the joint structure tolerances, surface roughness, and assembly equipment accuracy tolerance. Additionally, by creating only one shear layer (as shown in FIG. 2) the force required can be significantly reduced.

In addition, the use of various combinations of joint structure cross-section geometries allow for the optimization of the hermetic seal for specific applications. For example, a combination of a rectangular-shaped tongue joint structure joined together with a trapezoidal-shaped groove joint structure decreases the area in which the joining surfaces meet. In this embodiment, only the corners of the rectangular joint structure initiate shear. The initial area of local shear is much smaller than in an embodiment having a rectangular-shaped tongue joint structure and a rectangular-shaped groove joint structure. Thus, the force required to cold weld is reduced.

In another embodiment, the required force is reduced further if only one corner of the rectangular tongue joint structure initiates a shear force with the sloped trapezoidal groove joint structure. The force required to initiate plastic deformation on one corner of the rectangular tongue is half the force required to create the same pressure on two corners of the rectangular tongue.

In addition to joint design, the joining surface material composition and associated physical properties can have an effect on the force required to form the hermetic seal. For example, a joining structure material can have a low yield stress, which consequently makes the material easier to deform and makes it easier to expose clean bondable surfaces. Suitable joining surface materials with low yield stresses include, but are not limited to, indium, aluminum, gold, and tin. Conversely, impurities will act to increase the yield stress of the basic metal either by adding strain energy to the crystal structure or interfering with dislocation mobility. Therefore, increasing the material purity can reduce the yield stress. Exceptions may exist where the addition of a second material may lower the melting point and thus the overall yield stress is reduced because the ambient temperature is closer to the melting point.

Another physical property which affects the force required for cold welding is the hardness of a joining surface metal's oxide. Metals having a higher ratio between the oxide hardness and parent metal hardness require less deformation to cold weld. Conversely, soft metal oxides deform with the parent metal and do not fracture as easily thus maintaining the oxide barrier to cold weld bonding. Metals having a high oxide to parent metal hardness ratio include, but are not limited to, indium and aluminum. Since gold and platinum do not have an oxide under ambient conditions, the oxide hardness to parent metal hardness does not substantially affect the amount of force required to cold weld these metals. However, gold and platinum do have an adsorbed organic contaminant layer that acts as a barrier to cold weld bonding.

Furthermore, a joining surface metal's grain structure and inherent strain influence the yield strength. In polycrystalline metals, the yield stress is often described by the Hall-Petch relationship where the yield stress scales as one over the square root of the grain size. This relationship exists because the crystallographic slip plane in adjacent grains do not usually line up, so additional stress is required to activate a new slip plane in the adjacent grain. Therefore, by decreasing the number of grains (i.e., increasing the grain size) the yield stress can be lowered. Annealing the metal can lower the yield stress by increasing the grain size and decreasing the inherent strain in the metal. Annealing may also have other beneficial effects such as desorbing entrapped hydrogen from electroplated layers.

Finally, the bonding process can influence the force required to form the hermetic seal. In addition, minimizing the total amount of deformation will reduce the amount of strain hardening the joining surface material develops. For instance, shorter joint structures may develop less strain hardening since the total amount of deformation is reduced. In addition, the cold welding process time or strain rate may also have an effect on the strain hardening. The bonding time also may influence the amount of metal interdiffusion. See Takahashi & Matsusaka, "Adhesional bonding of fine gold wires to metal substrates," *J. Adhesion Sci. Technol.*, 17(3): 435-51 (2003).

Figure 22:
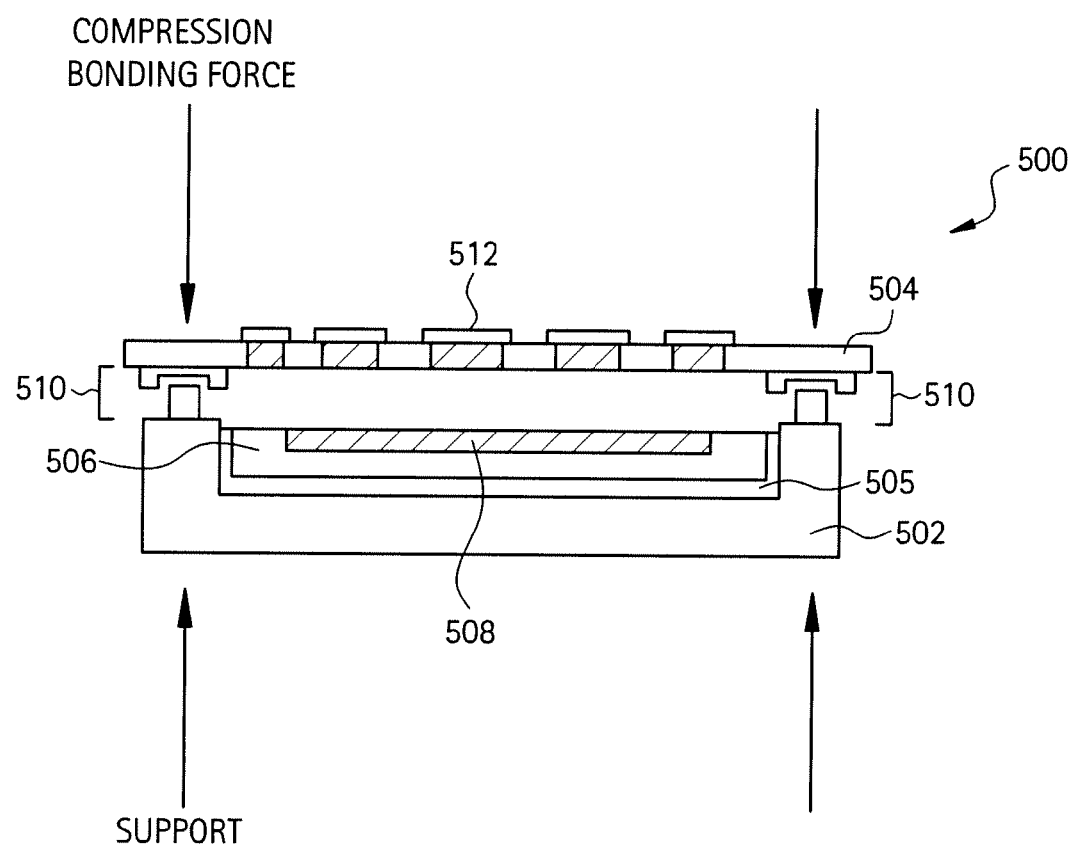
FIG. 22 is a cross-sectional view of one embodiment of a sealed structure using a bonded "sandwich" structure to protect an intermediate substrate which is not subjected to compressive bonding forces.

In sealing with a compression force, it may be desirable to align the support force with the compressive force, in order to avoid a cantilever type force on one of the substrates that might result in fracture of some substrate materials. In one embodiment, this may be accomplished by inserting a first substrate, which is to be protected from the compression forces, within at least two other substrate structures, which are then sealed together, e.g., by cold welding as described herein. In a preferred embodiment, at least one of the two other substrate structures includes a cavity or recess suitable for cradling or otherwise holding the first substrate. The at least two other substrate structures have joint structures which can be compressed together to trap the first substrate in a cavity defined between the at least two other substrate structures. FIG. 22 illustrates one embodiment of such as sealing approach. Sealed device 500 includes a sensor substrate 506 which has fabricated thereon a biosensor 508. The sensor substrate is placed in cavity 505 in base substrate 502. Upper substrate 504, which includes reservoir caps/openings 512, is bonded to base substrate 502 by a compression cold welding process applied at joint structures 510. In another embodiment, the third, or "sensor," substrate has a different secondary device on it, instead of a sensor. For example, the third substrate may include a MEMS device, such as a gyroscope, resonator, etc. The device could be sealed under vacuum.

Compressed Gasket Approach

Figure 15:
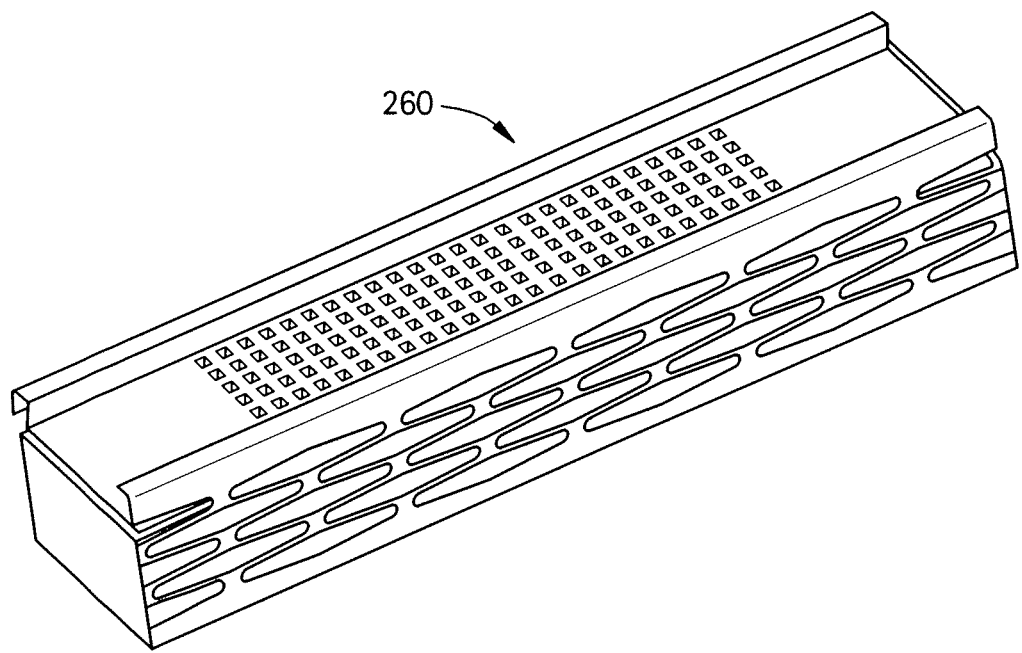
FIG. 15 is a perspective view of one embodiment of a hermetic seal system having a Nitinol clamp.

In another aspect, a compression seal is formed in the absence of metal-to-metal bonding. In this case, the parts may require a permanent joining force to remain hermetic. The joining force can be applied through a variety of clamping mechanisms. In one embodiment, a Nitinol, or other shape memory alloy, clamp can be fashioned to provide a loose fit around the substrates until they are aligned, after which the Nitinol can be heated past its phase transition point causing it to clamp down onto the substrates as shown in FIG. 15. This phase transition temperature can be controlled (by varying the composition of the shape memory alloy). Therefore, device assembly can occur at sub-phase transition temperatures, then the assembly is warmed to the phase transition temperature and the clamping mechanism is activated.

In another embodiment, a metal or plastic clamp can be elastically deformed to allow the substrates of a hermetic seal system to be mounted where the clamp's zero stress configuration is significantly smaller than the joining substrates. Once the joining substrates are aligned between the clamp, all forces on the clamp can be removed allowing it to squeeze the joining substrates. Other fasteners including screws, rivets, solders, heat shrinking polymers, opposed magnets, and the like, can be fashioned to clamp the substrates. The clamp should be able to permanently apply a force while minimizing the additional size of the joining pair.

Figure 16A:
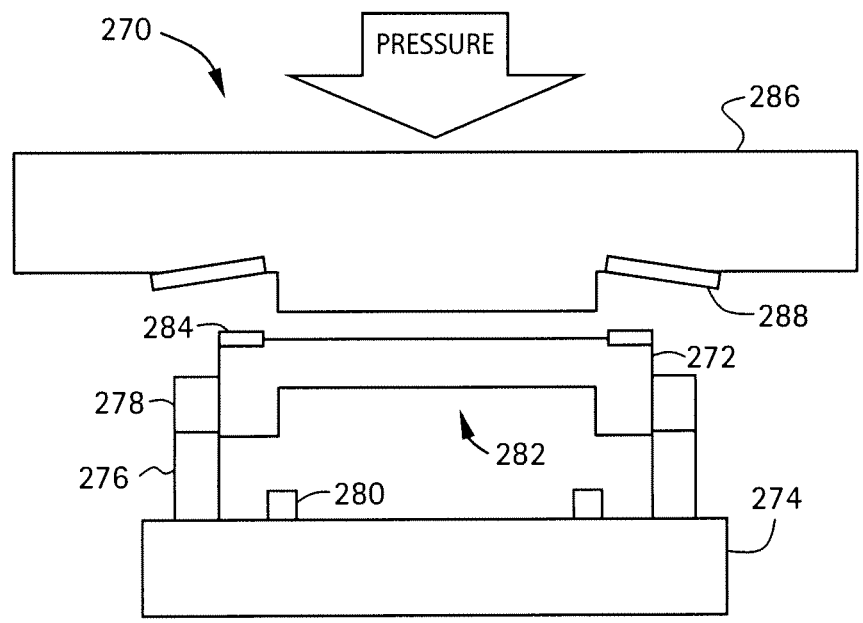
FIGS. 16A-C are cross-sectional views of one embodiment of a hermetic seal system having a solder clamp, showing the assembly steps.
Figure 16B:
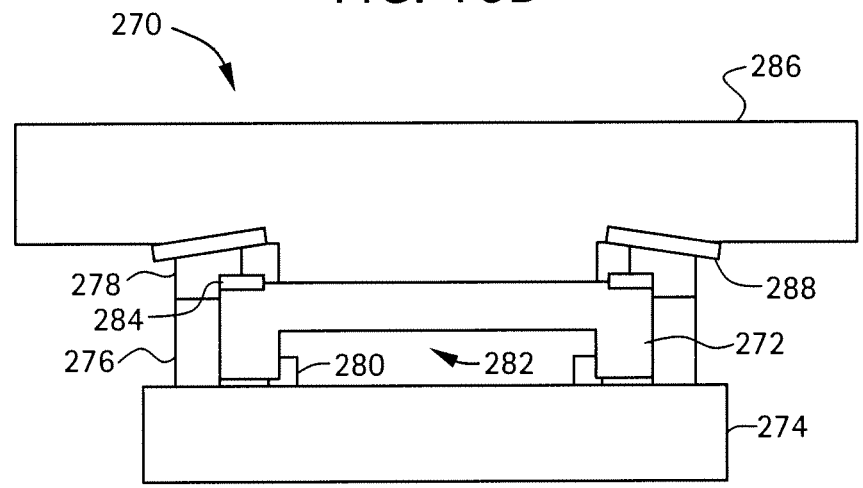
Figure 16C:
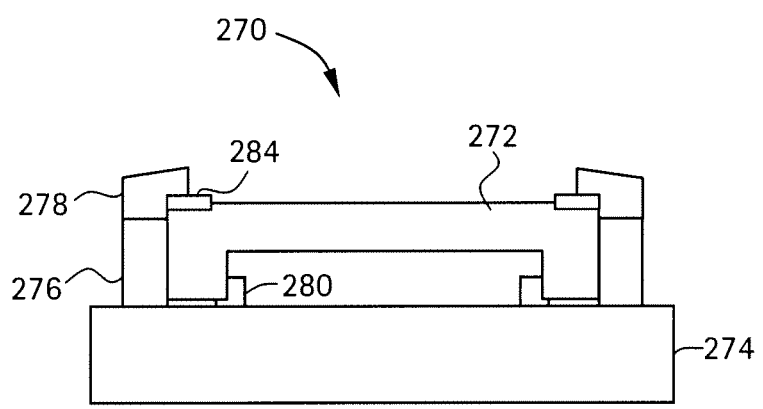

An embodiment of a hermetic seal system 270 having a solder clamp is illustrated in FIGS. 16A-C. In FIG. 16A, the hermetic seal system 270 comprises posts 276 which are attached, plated or micro-machined onto a second substrate 274. Solder 278 is patterned on top of the posts 276. Second joint structures 280 on the second substrate 274 are aligned to overlap a groove joint structure 282 on the first substrate 272. Pads 284 comprising metal are deposited onto the top of the first substrate 272. A heater plate 286 containing heaters 288 is aligned with the solder 278 on top of the posts 276 and overlapping onto the metal pads 284 on the first substrate 272.

As illustrated in FIG. 16B, the heater plate 286 presses the first and second substrates 272 and 274 together, creating a seal between the first joint structures 280 and the overlapping groove joint structure 282. As the heater plate 286 presses down, the heaters 288 are pulsed to reflow the solder 278 so that the solder reflows onto the metal pads 284 on the first substrate 272. The heater plate 286 may then be removed once the solder 278 solidifies. FIG. 16C illustrates the hermetic seal system 270 after removal of the heater plate 286 and after formation of the solder clamp and hermetic seal.

In an alternate embodiment (not shown), the heater plate 286 may be coated with materials that can tolerate the heater temperature used and that act as a poor surface for the solder 278 to bond to, depending on the solder used. In such an embodiment, the heater plate 286 may be removed once the solder 278 solidifies without the solder bonding to the heaters 288. In addition, the thickness of reflowed solder 278 onto the metal pads 284 may be adjusted depending on the desired strength of the solder clamp.

The cold welding sealing features of the present invention may also be employed to form a clamp for a compressive hermetic seal. FIG. 17 illustrates an embodiment of a hermetic seal system 290 where a tongue and groove joint structure design is used to clamp a compression seal material 306 between two substrates 292 and 294 and create a compression hermetic seal. The first joint structure 296a/296b comprises the groove portion of the joint structure design. The tongue portion of the joint structure design comprises a heater 300 on the second substrate 294, a intermediate layer 302 on the heater, and a joining surface material 304 on the intermediate layer. The compression seal material 306 has a round cross-section and is disposed on the second substrate 294 between the tongue and groove clamp at the edge of the substrates. The groove joint structure of the first substrate 292 is then joined to the tongue joint structure of the second substrate 294 using thermocompression bonding, clamping the compression seal material between the substrates and forming a hermetic seal. It should be clear that any of the features described for cold welding may be used to create a cold weld clamp without the addition of heat. A cold weld clamp would not have the requirement of a closed geometry since its main function is to clamp two substrates together, not create a seal.

In another embodiment (not shown), the compression seal material may be disposed on the second substrate on the edges of the second substrate, outside the tongue and groove clamp. It should be understood however, that the stresses on the substrate materials will differ depending on the placement of the compression seal material.

Depending on the application, compliant polymers may replace any of the metal joint structures and joining surfaces in the embodiments described above. Although the sealing mechanism for sealing compliant polymers is not defined as cold welding, the effect of isolating a reservoir or cavity from adjacent cavities or external contamination with seals is the same. Compliant polymers can require significantly less pressure to create a seal than the pressure required to create plastic deformation in a cold weld process. Traditionally compliant polymers have been poor choices to seal in applications where water permeation is critical. However, recent advances in polymer chemistry have produced polymers that have been modified to significantly reduce water permeation by the addition of metal, or ceramic particles. For example, an epoxy modified by the addition of carbon nanoparticles has a reported water permeation rate an order of magnitude lower than conventional epoxies. Compliant polymer seals require selection of low Young's modulus polymers and minimization of the surface contact area to provide seals using low compressive forces. In addition, increasing the number of circumscribed joint structures may create pockets which act to significantly slow water permeation through the seals.

The above described embodiments and examples can be practiced using a single joint structure design or multiple redundant, joint structures to mitigate potential fabrication defects that may result in one or more of the redundant joint structures leaking. Additionally, multiple joining surfaces act to increase the seal path length and therefore increase the force required to form a seal. The number of redundant joint structures needs to be balanced with the strength of the substrate materials, the force required to cold weld them, and any residual stresses that remain in the substrate after the cold weld process, including stresses applied by any clamping features.

Applications of the Hermetically Sealed Devices and Methods

The cold welding technique has a number of advantages in terms of both processing and manufacturability. First, the sealing features are amenable to standard MEMs processes and can be incorporated monolithically into the MEMs device. Second, an array of closely spaced reservoirs can be sealed simultaneously. In fact, entire wafers of devices can be sealed simultaneously in a wafer-to-wafer bonding process. Multiple wafers can be sequentially or simultaneously bonded one on top of the other so that a cold weld is made on each surface of the internal wafers. In addition, active devices can be integrated with passive devices by passing feed-throughs under the sealing features. Finally, since the process does not involve heat, temperature sensitive materials can be packaged in the reservoir volume. Temperature sensitive materials may include volatile liquids, organic chemicals, drugs, explosive gases, chemical sensors, and sensitive electronics.

Figure 18:
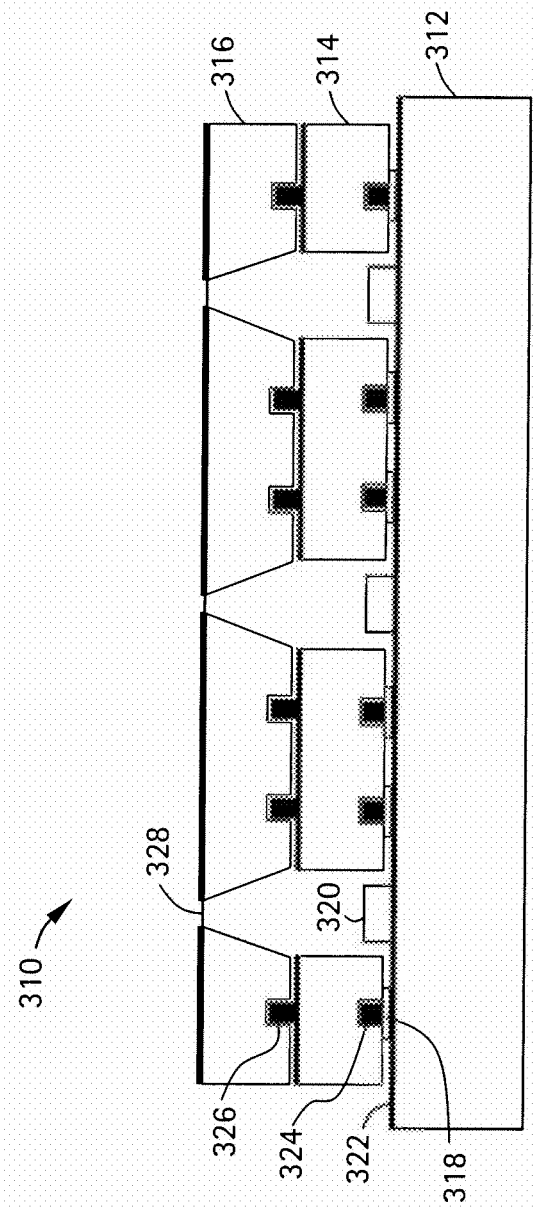
FIG. 18 is a cross-sectional view of one embodiment of a device that includes an array of reservoirs that have each been individually hermetically sealed use a compression cold welding process with a tongue and groove joint design. The body of the device in which the reservoirs are defined comprises two substrate portions that also have been hermetically sealed together using a compression cold welding process with a tongue and groove joint design.

FIG. 18 illustrates an embodiment of active and passive wafers cold welded together to form an array of hermetically sealed devices 310. The array of hermetically sealed devices 310 represents one die that was cold welded simultaneously as part of an array of die on the same wafer. A first active layer 312 comprises sensors 320, a gold electrical trace layer 322, dielectric layers 318, and tongue joint structures 324. Dielectrics between the active layer substrates and any electrical trace layers are omitted for simplicity. These tongue joint structures 324 comprise gold and are cold welded to a passive layer 314 having a groove joint structures into which the first tongue joint structures are compressed. The passive layer 314 comprises a metallization layer having second tongue joint structures 326 and openings which are aligned with the sensors 320 on the first active layer 312. The second tongue joint structures 326 are cold welded to a groove joint structure in a second active layer 316. The second active layer comprises openings which are aligned with the sensors 320 on the first active layer. In addition, the second active layer comprises a metallization layer having reservoir caps 328. Thus, the array of hermetically sealed devices 310, as illustrated in FIG. 18 has separated the sensors 320 from each other and from the environment with hermetic seals. However, the reservoir caps 328 may be later opened to expose the sensors 320 to the environment. Electrical connections to the active component 320 may be achieved using vias depending upon the substrate material and fabrication limitations.

Figure 19:
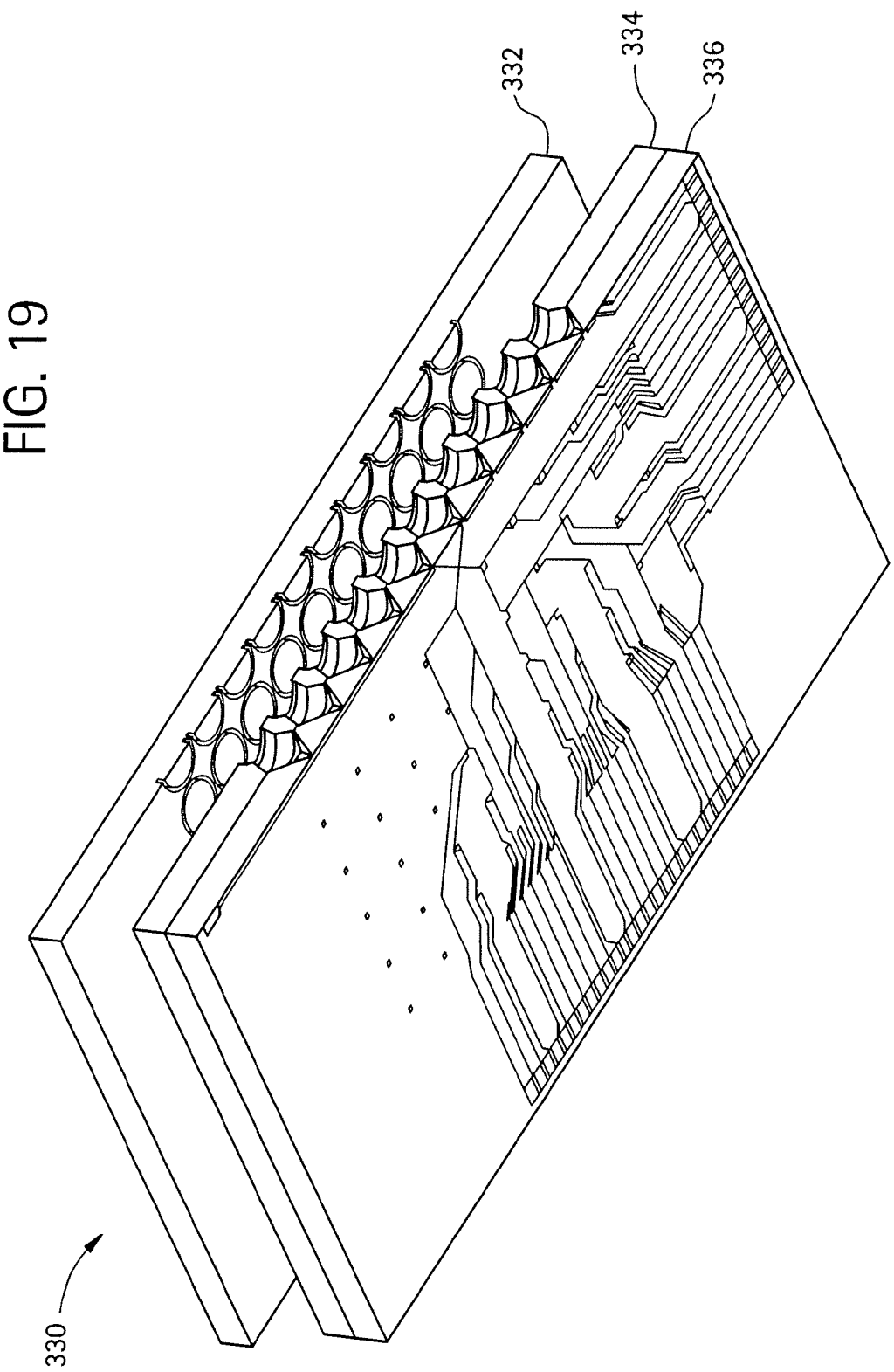
FIG. 19 is a perspective view of one embodiment of a device that includes an array of reservoirs and having a joint design for individually hermetically sealing the reservoirs using a compression cold welding process.

FIG. 19 illustrates a perspective view of an embodiment of a multi-reservoir drug delivery chip having an first active layer 332, a passive layer 334, and a second active layer 336. Layers 332 and 334, which are shown separated to illustrate the joint structures on layer 332, are (to be) bonded by compression cold welding. (Layers 334 and 336 need not be bonded by any particular technique.)

In an implanted medical sensor application, a compliant polymer may be patterned on each substrate. The polymer can be patterned using conventional MEMs techniques such as molding (e.g., PDMS soft lithography), photolithography (e.g., photo-definable silicone), stereolithography, selective laser sintering, inkjet printing, deposition and reflowed, or etched (e.g., $O_2$ plasma etching). Alternatively, the polymer can be patterned and metallized prior to placing it in between the opposing substrate.

Figure 20:
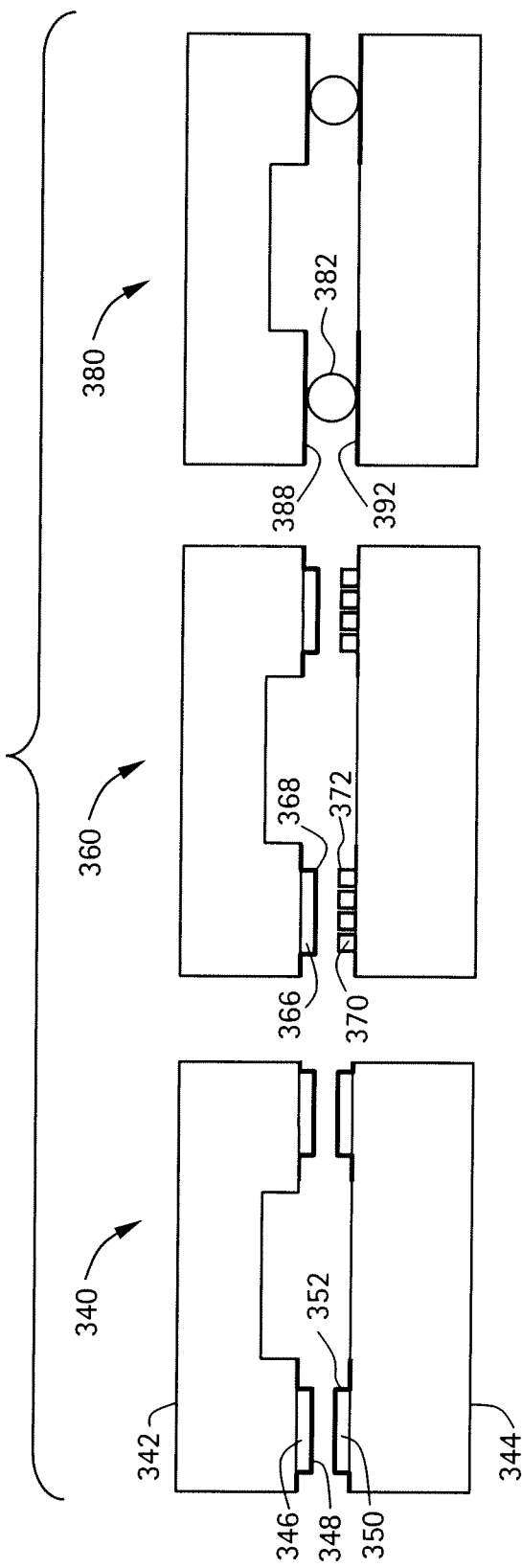
FIG. 20 is cross-sectional views of three embodiments of hermetic seal systems having various polymer joint structures plated with metal joining surfaces.

FIG. 20 illustrates various embodiments of hermetic seal systems having various polymer joint structures 346, 350, 366, 370, 382 with a deposited metal joining surfaces 348, 352, 368, 372, 383, 388, 392. In this case, metal-metal bonds are not formed by shear deformation, but by the mechanism detailed in Ferguson et al. Hermetic seal system 340 maximizes the contact area and leak path length. Hermetic seal system 360 minimizes the contact area to increase the local pressure when displacing the surface contaminants during cold welding. Hermetic seal system 380 comprises a polymer pre-form 382 that is not fabricated onto a substrate. The pre-form includes a metallized surface 383. Hermetic seal system 380 may be characterized as a metallized gasket seal system.

In certain embodiments, acoustic (e.g., ultrasound) or laser energy can be used in a process to bond a metal with a polymer. This application of acoustic or laser energy can be applied to methods which bond a metal layer/coating onto a polymeric substrate, or alternatively, bond a polymeric coating/layer onto a metal substrate. Examples of polymeric materials in these embodiments include fluoropolymers, such as expanded polytetrafluoroethylene (ePTFE), or a liquid crystalline polymer. In one embodiment, a liquid crystalline polymeric substrate (e.g., certain hermetic LC polyesters) is bonded to another liquid crystalline polymeric substrate, or it is metallized and the metallized surface is bonded to another liquid crystalline polymeric substrate or another metallized surface.

In further or alternative embodiments, the sealing concepts described in U.S. Patent Application Publication No. 2002/0179921 A1 to Cohn can be adapted for use in the hermetic sealing of implantable drug delivery or analyte sensing applications described herein and in U.S. Pat. Nos. 5,797,898, 6,527,762, 6,491,666, and 6,551,838, and U.S. Patent Application Publication Nos. 2004/0121486 A1, 2004/0127942 A1, and 2004/0106953 A1.

The devices described herein can be used with or incorporated into a variety of devices, including implantable medical devices and other devices. Examples include drug delivery devices, diagnostic and sensing devices, some of which are described in U.S. Pat. No. 5,797,898, 6,551,838, 6,527,762, as well as in U.S. Patent Application Publications No. 2002/0099359, No. 2003/0010808, No. 2004/0121486, which are incorporated herein by reference.

FIG. 21 illustrates a cross-sectional view of one embodiment of a microchip device before and after the open reservoirs are sealed using cold welding. Device substrate 402 has reservoirs 404, loaded with reservoir contents 406. The reservoirs 404 are closed off on the front side 401 of the substrate 402 by reservoir caps 408. The back side surface of the substrate 402 has one tongue joint structure 414 on each side of each reservoir 404. A sealing substrate 410 is positioned over the back side 403 of the device substrate 402 over the open reservoirs 404. The sealing substrate 410 has groove joint structures 412a/412b aligned to the tongue joint structures 414. The sealing substrate may be transparent to optical wavelengths from visible to infrared by selecting an appropriate material. In this way the reservoir contents may be optically probed. The two substrates are then joined together and cold welding at the tongue and groove joint structures 414/412a and 412b creates hermetic seals separating the individual reservoirs 404 from one another and from the environment.

In some embodiments, the hermetically sealed device described herein is a subcomponent of another device. For example, it may be part of an implantable drug delivery device that further comprises a sensor indicative of a physiological condition of a patient, an electrode for providing electrical stimulation to the body of a patient, a pump, a catheter, or a combination thereof. Examples of some of these are described in U.S. Patent Application Publications No. 2004/0127942 A1 and No. 2004/0106953 A1, and in U.S. Pat. No. 6,491,666, which are incorporated herein by reference.

Electrical Vias and Wire Connections Made by Compression Cold Welding

In another aspect, the compression cold welding techniques described herein are adapted to create highly reliable, low resistance electrical connections without heat. In one embodiment, the bond structure formed by compression cold welding provides simultaneously a mechanical securement means and a continuous electrical conducting path.

Figure 23:
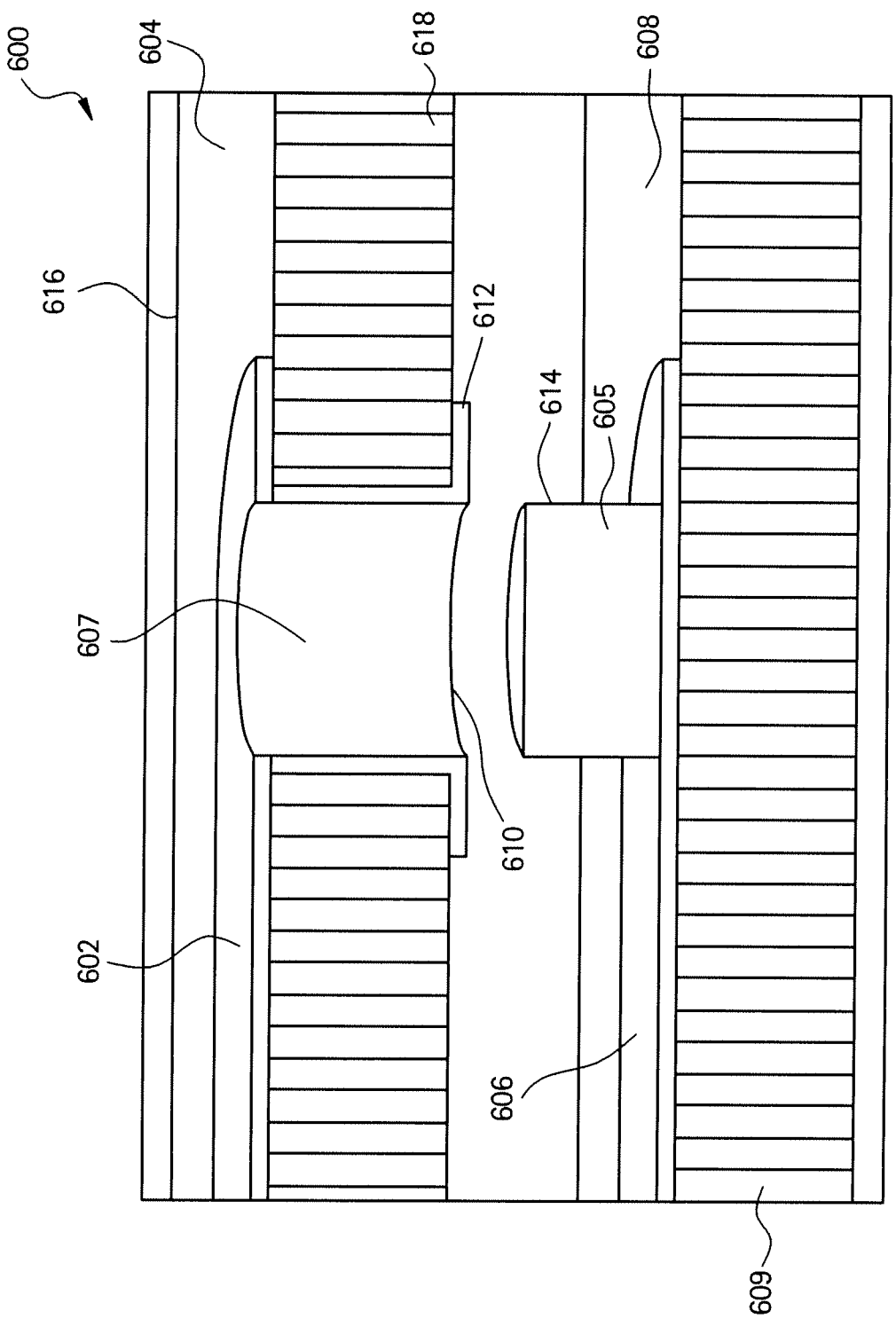
FIG. 23 is cross-sectional view of one embodiment of parts, prior to bonding, for forming an electrical via connection by compression cold welding as described herein.

One embodiment of an electrical via connection 600 is shown in FIG. 23. A first metal layer 602 on a first surface 604 of first substrate 618 is to be electrically connected to a second metal layer 606 on a surface 608 of second substrate 609. Metal deposited on the inside of the seal feature 610 on the first substrate creates electrical contact between the first metal layer 602 and the first joining surface 612. The second joining surface 614 may be formed by electroplating a tooth 605 on the second metal layer 606. The width of the tooth exceeds the width of the metallized hole by between 1-50 um. The cross section of the seal structure 610 through substrate 604 is shown to be rectangular, but it may be any shape that can be fabricated using micromachining or MEMs processes to maximize coverage of deposited material and reduce residual stresses in the joint. When the joining surfaces 612 and 614 are aligned and the substrates 618 and 609 are compressed together, shear at the joining interface exposes clean metal on both joining surfaces, creating a cold weld bond. The resulting bond creates a low resistance electrical connection between the first metal layer 602 and the second metal layer 606.

It should be understood that this technique is not limited to an electroplated ridge of a particular metal or alloy or shape. The ridge cross-section in the plating direction may be rectangular (as shown), hemispherical, triangular, trapezoidal—any shape appropriate to create a cold weld joint as described herein. Any of the conductive materials described herein may be considered for use as joining materials including metals or conductive polymers with appropriate mechanical and electrical properties to create electrical connection by elastic compression rather than cold welding. The second joining structure may have a core that is a different material than, or the same as, the material of the joining surface. All the sealing features described herein for creating cold weld joints may be used to create electrical connections as well.

Multiple electrical connections may be created in a small area using traditional MEMS processes and/or micromachining to deposit and pattern metal and to create vias through the substrates. The electrical connection features described herein may be included on substrates with seal features such that the electrical connections are created simultaneously with the hermetic seal when two opposing substrates are compressed together.

In another embodiment, it may be advantageous to have sloped side walls on the first joining surface 612 to more easily accommodate deposition of the first joint surface 612. Furthermore, material deposition may occur on both sides 616 and 618 of the first substrate 604. This is one method of ensuring proper material deposition throughout the via hole 607.

Figure 25:
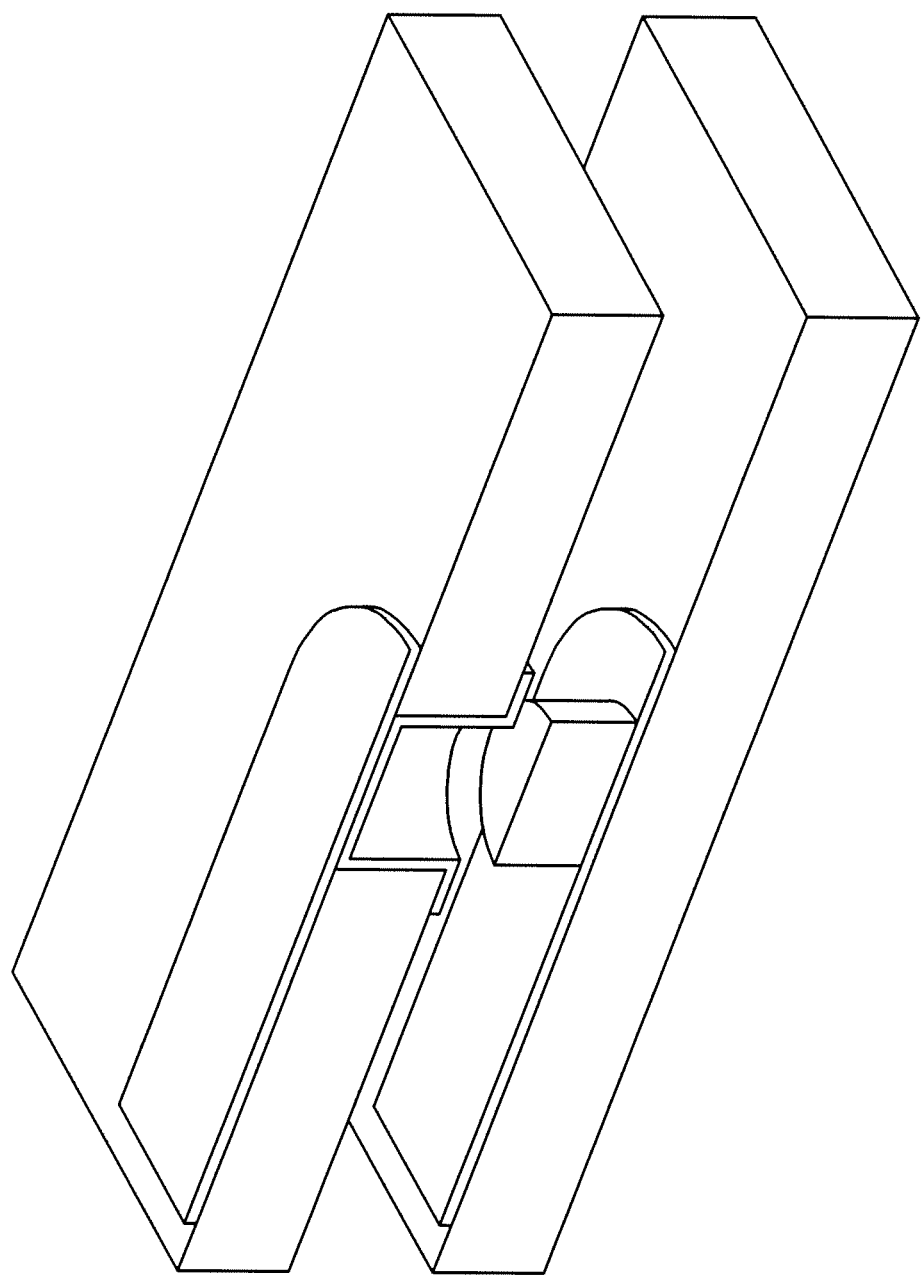
FIG. 25 is a perspective, cross-sectional view of one embodiment of parts, prior to bonding, for forming an electrical via connection by compression cold welding.
Figure 26:
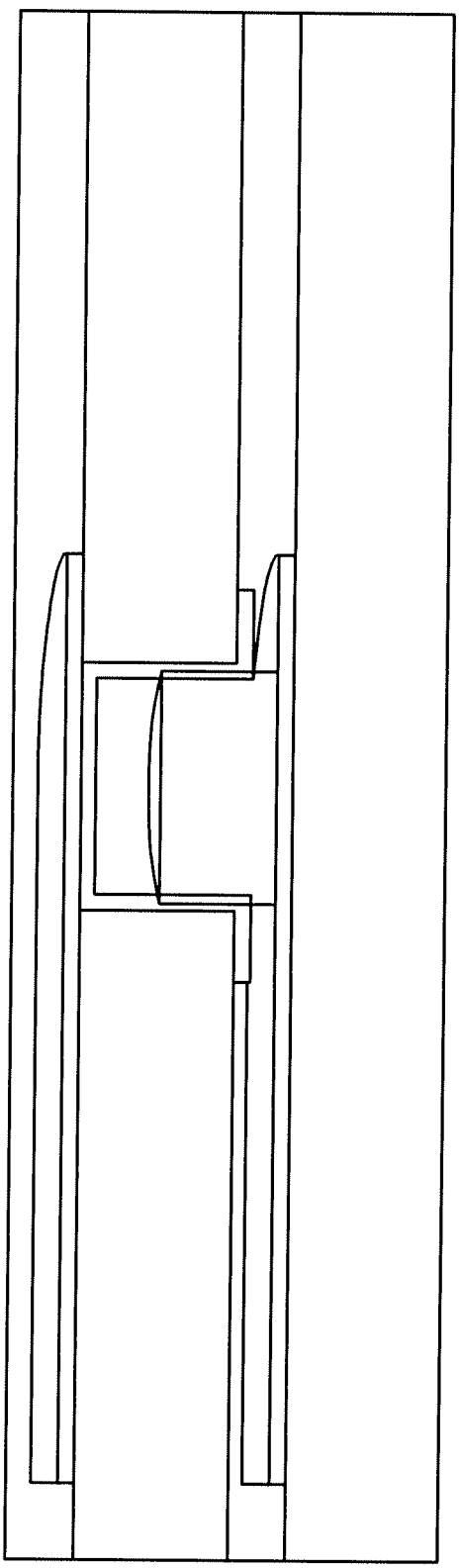
FIG. 26 is a perspective view of one embodiment of an electrical via connection made by compression cold welding. The illustration shows the material overlap between the aperture and tooth.

FIGS. 25 and 26 further illustrate possible embodiments for electrical vias made by compression cold welding.

Figure 24A:
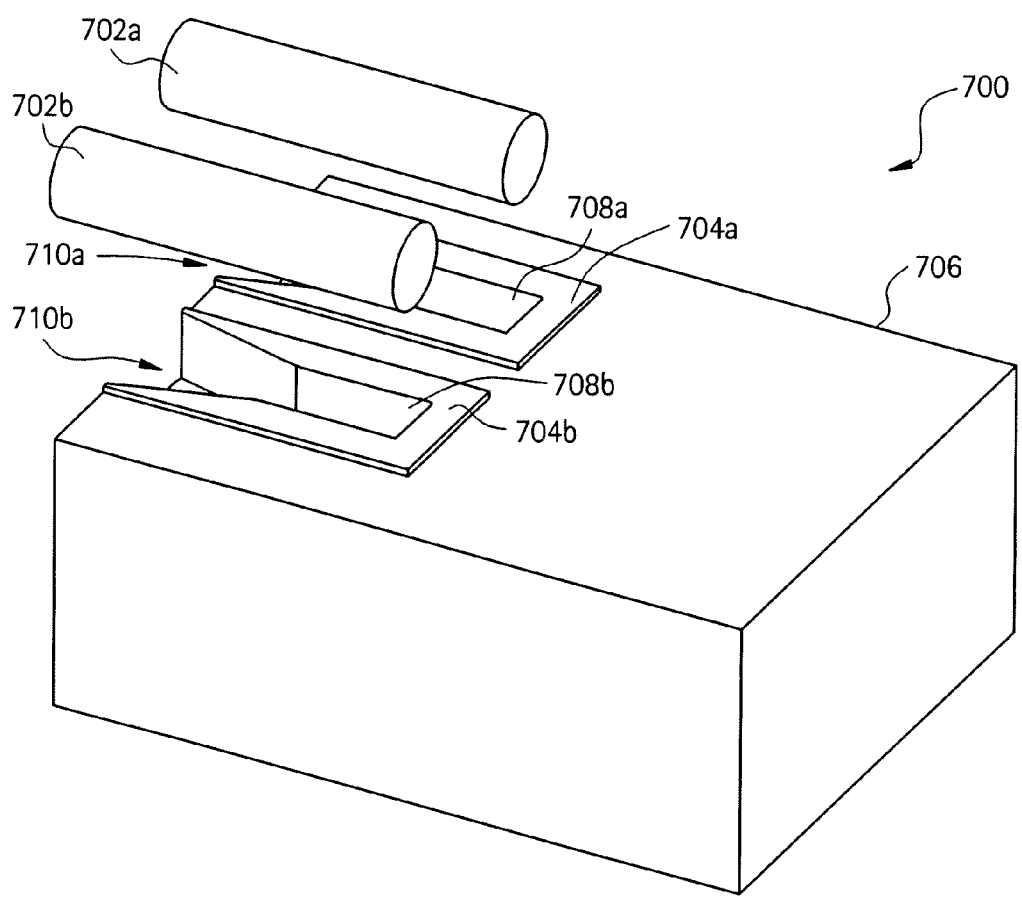

One embodiment of an electrical wire connection 700 is shown in FIGS. 24A-B. Conductive leads 702a, 702b are to be electrically connected to traces 704a, 704b, respectively, on substrate 706. Each conductive lead 702a, 702b has a diameter greater than joining surface widths 708a, 708b and are aligned and pressed into seal features 710a, 710b. Seal features 710a, 710b may be formed by etching trenches into substrate 706 and then depositing a metal layer 704a, 704b in them. The trenches are wider at one end, which provides space to appropriately relieve strain in the conductive leads 702a, 702b using epoxy, silicone, solder, or other polymeric material. The space also allows the leads to lay parallel to the top surface of substrate 706 even though a smaller area of the trench is used to create the cold weld to the conductive leads.

The leads are shown having a circular cross section; however, any cross-section suitable to forming a cold weld or compressive seal as described herein may be used. The cross section of the seal structures 710a, 710b through substrate 710a, 710b is shown to be rectangular, but it may be any shape that can be fabricated using micromachining processes or MEMs processes to maximize coverage of deposited material and reduce residual stresses in the joint.

In alternative embodiments, electrical connections may be created using the elastic properties of the conductive leads and/or the conductive layers 704a, 704b rather than a cold weld to cause a press fit or friction fit capture.

The conductive leads may be formed of a single material, multiple layers of different materials, and/or coated with an electrical insulation layer. Local shear may sufficiently deform the insulation layer to expose the conductive leads underneath and create a cold weld or compressive electrical connection.

In alternate embodiments, non-metal conductive materials, such as a silver impregnated polymer, may be used in place of metal layers in the via or wire connections described above. In a preferred embodiment, the materials of construction are biocompatible and biostable.

Further Details of the Multi-Cap Reservoir Devices

Substrate and Reservoirs

In one embodiment, the containment device comprises a body portion, i.e., a substrate, that includes one or more reservoirs for containing reservoir contents sealed in a fluid tight or hermetic manner. As used herein, the term "hermetic" refers to a seal/containment effective to keep out helium, water vapor, and other gases. As used herein, the term "fluid tight" refers to a seal/containment which is not gas hermetic, but which are effective to keep out dissolved materials (e.g., glucose) in a liquid phase. The substrate can be the structural body (e.g., part of a device) in which the reservoirs are formed, e.g., it contains the etched, machined, or molded reservoirs.

In preferred embodiments, the reservoirs are discrete, non-deformable, and disposed in an array across one or more surfaces (or areas thereof) of the device body. As used herein, the term "reservoir" means a well, a cavity, or a hole suitable for storing, containing, and releasing/exposing a precise quantity of a material, such as a drug formulation, or a secondary device, or subcomponent. The interconnected pores of a porous material are not reservoirs. In a one embodiment, the device includes a plurality of the reservoirs located in discrete positions across at least one surface of the body portion. In another embodiment, there is a single reservoir per each reservoir substrate portion; optionally two or more of these portions can be used together in a single device.

Reservoirs can be fabricated in a structural body portion using any suitable fabrication technique known in the art. Representative fabrication techniques include MEMS fabrication processes, microfabrication processes, or other micromachining processes, various drilling techniques (e.g., laser, mechanical, and ultrasonic drilling), and build-up or lamination techniques, such as LTCC (low temperature co-fired ceramics). The surface of the reservoir optionally can be treated or coated to alter one or more properties of the surface. Examples of such properties include hydrophilicity/hydrophobicity, wetting properties (surface energies, contact angles, etc.), surface roughness, electrical charge, release characteristics, and the like. MEMS methods, micromolding, micromachining, and microfabrication techniques known in the art can be used to fabricate the substrate/reservoirs from a variety of materials. Numerous other methods known in the art can also be used to form the reservoirs. See, for example, U.S. Pat. No. 6,123,861 and U.S. Pat. No. 6,808,522. Various polymer forming techniques known in the art also may be used, e.g., injection molding, thermocompression molding, extrusion, and the like.

In various embodiments, the body portion of the containment device comprises silicon, a metal, a ceramic, a polymer, or a combination thereof. Examples of suitable substrate materials include metals (e.g., titanium, stainless steel), ceramics (e.g., alumina, silicon nitride), semiconductors (e.g., silicon), glasses (e.g., Pyrex™, BPSG), and degradable and non-degradable polymers. Where only fluid tightness is required, the substrate may be formed of a polymeric material, rather than a metal or ceramic which would typically be required for gas hermeticity.

In one embodiment, each reservoir is formed of (i.e., defined in) hermetic materials (e.g., metals, silicon, glasses, ceramics) and is hermetically sealed by a reservoir cap. Desirably, the substrate material is biocompatible and suitable for long-term implantation into a patient. In a preferred embodiment, the substrate is formed of one or more hermetic materials. The substrate, or portions thereof, may be coated, encapsulated, or otherwise contained in a hermetic biocompatible material (e.g., inert ceramics, titanium, and the like) before use. Non-hermetic materials may be completely coated with a layer of a hermetic material. For example, a polymeric substrate could have a thin metal coating. If the substrate material is not biocompatible, then it can be coated with, encapsulated, or otherwise contained in a biocompatible material, such as poly(ethylene glycol), polytetrafluoroethylene-like materials, diamond-like carbon, silicon carbide, inert ceramics, alumina, titanium, and the like, before use. In one embodiment, the substrate is hermetic, that is impermeable (at least during the time of use of the reservoir device) to the molecules to be delivered and to surrounding gases or fluids (e.g., water, blood, electrolytes or other solutions).

The substrate can be formed into a range of shapes or shaped surfaces. It can, for example, have a planar or curved surface, which for example could be shaped to conform to an attachment surface. In various embodiments, the substrate or the containment device is in the form of a planar chip, a circular or ovoid disk, an elongated tube, a sphere, or a wire. The substrate can be flexible or rigid. In various embodiments, the reservoirs are discrete, non-deformable, and disposed in an array across one or more surfaces (or areas thereof) of an implantable medical device.

The substrate may consist of only one material, or may be a composite or multi-laminate material, that is, composed of several layers of the same or different substrate materials that are bonded together. Substrate portions can be, for example, silicon or another micromachined substrate or combination of micromachined substrates such as silicon and glass, e.g., as described in U.S. Patent Application Publication 2005/0149000 or U.S. Pat. No. 6,527,762. In another embodiment, the substrate comprises multiple silicon wafers bonded together. In yet another embodiment, the substrate comprises a low-temperature co-fired ceramic (LTCC) or other ceramic such as alumina. In one embodiment, the body portion is the support for a microchip device. In one example, this substrate is formed of silicon.

In one embodiment, either or both substrates to be bonded may be formed of one or more glasses, which may be particularly useful in embodiments where it is desirable to view or interrogate an object or material that is contained between the sealed substrates, e.g., in a cavity or reservoir. That is, where the substrate can serve as an fluid-tight window. Representative examples of glasses include aluminosilicate glass, borosilicate glass, crystal glasses, etc.

Total substrate thickness and reservoir volume can be increased by bonding or attaching wafers or layers of substrate materials together. The device thickness may affect the volume of each reservoir and/or may affect the maximum number of reservoirs that can be incorporated onto a substrate. The size and number of substrates and reservoirs can be selected to accommodate the quantity and volume of reservoir contents needed for a particular application, manufacturing limitations, and/or total device size limitations to be suitable for implantation into a patient, preferably using minimally invasive procedures.

In a preferred embodiment for an implantable sensor application using a planar sensor, the substrate preferably is relatively thin, as noted above.

The substrate can have one, two, three or more reservoirs. In various embodiments, tens, hundreds, or thousands of reservoirs are arrayed across the substrate. For instance, one embodiment of an implantable drug delivery device includes between 250 and 750 reservoirs, where each reservoir contains a single dose of a drug for release. In one sensing embodiment, the number of reservoirs in the device is determined by the operation life of the individual sensors. For example, a one-year implantable glucose-monitoring device having individual sensors that remain functional for 30 days after exposure to the body would contain at least 12 reservoirs (assuming one sensor per reservoir). In another sensor embodiment, the distance between the sensor surface and the reservoir opening means is minimized, preferably approaching a few microns. In this case, the volume of the reservoir is primarily determined by the surface area of the sensor. For example, the electrodes of a typical enzymatic glucose sensor may occupy a space that is 400 µm by 800 µm.

In one embodiment, the reservoirs are microreservoirs. The "microreservoir" is a reservoir suitable for storing and releasing/exposing a microquantity of material, such as a drug formulation. In one embodiment, the microreservoir has a volume equal to or less than 500 µL (e.g., less than 250

μL, less than 100 μL, less than 50 μL, less than 25 μL, less than 10 μL, etc.) and greater than about 1 nL (e.g., greater than 5 nL, greater than 10 nL, greater than about 25 nL, greater than about 50 nL, greater than about 1 μL, etc.). The term "microquantity" refers to volumes from 1 nL up to 500 μL. In one embodiment, the microquantity is between 1 nL and 1 μL. In another embodiment, the microquantity is between 10 nL and 500 nL. In still another embodiment, the microquantity is between about 1 μL and 500 μL. The shape and dimensions of the microreservoir can be selected to maximize or minimize contact area between the drug material (or sensor or other reservoir contents) and the surrounding surface of the microreservoir.

In one embodiment, the reservoir is formed in a 200-micron thick substrate and has dimensions of 1.5 mm by 0.83 mm, for a volume of about 250 nL, not counting the volume that would be taken up by the support structures, which may be about 20 to about 50 microns thick.

In another embodiment, the reservoirs are macroreservoirs. The "macroreservoir" is a reservoir suitable for storing and releasing/exposing a quantity of material larger than a microquantity. In one embodiment, the macroreservoir has a volume greater than 500 μL (e.g., greater than 600 μL, greater than 750 μL, greater than 900 μL, greater than 1 mL, etc.) and less than 5 mL (e.g., less than 4 mL, less than 3 mL, less than 2 mL, less than 1 mL, etc.).

Unless explicitly indicated to be limited to either micro- or macro-scale volumes/quantities, the term "reservoir" is intended to encompass both.

In one embodiment, the device comprises a microchip chemical delivery device. In another embodiment, the device includes polymeric chips or devices composed of non-silicon based materials that might not be referred to as "microchips." In one embodiment, the device comprises an osmotic pump, for example, the DUROS™ osmotic pump technology (Alza Corporation) included in commercial devices such as a VIADUR™ implant (Bayer Healthcare Pharmaceuticals and Alza Corporation).

Reservoir Cap Supports

Reservoir cap supports can comprise substrate material, structural material, or coating material, or combinations thereof. Reservoir cap supports comprising substrate material may be formed in the same step as the reservoirs. The MEMS methods, microfabrication, micromolding, and micromachining techniques mentioned above could be used to fabricate the substrate/reservoirs, as well as reservoir cap supports, from a variety of substrate materials. Reservoir cap supports comprising structural material may also be formed by deposition techniques onto the substrate and then MEMS methods, microfabrication, micromolding, and micromachining techniques. Reservoir cap supports formed from coating material may be formed using known coating processes and tape masking, shadow masking, selective laser removal techniques, or other selective methods.

A reservoir may have several reservoir cap supports in various configurations over its reservoir contents. For example, one reservoir cap support may span from one side of the reservoir to the opposite side; another reservoir cap support may cross the first reservoir cap support and span the two other sides of the reservoir. In such an example, four reservoir caps could be supported over the reservoir.

In one embodiment for a sensor application (e.g., a glucose sensor), the reservoir (of a device, which can include only one or which may include two or more reservoirs) has three or more reservoir openings and corresponding reservoir caps.

The dimensions and geometry of the support structure can be varied depending upon the particular requirements of a specific application. For instance, the thickness, width, and cross-sectional shape (e.g., square, rectangular, triangular) of the support structures may be tailored for a particular drug release kinetics for a certain drug formulation or implantation site, etc.

Reservoir Contents

The reservoir contents are essentially any object or material that needs to be isolated (e.g., protected from) the environment outside of the reservoir until a selected point in time, when its release or exposure is desired. In various embodiments, the reservoir contents comprise (a quantity of) chemical molecules, a secondary device, or a combination thereof.

Proper functioning of certain reservoir contents, such as a catalyst or sensor, generally does not require release from the reservoir; rather their intended function, e.g., catalysis or sensing, occurs upon exposure of the reservoir contents to the environment outside of the reservoir after opening of the reservoir cap. Thus, the catalyst molecules or sensing component can be released or can remain immobilized within the open reservoir. Other reservoir contents such as drug molecules often may need to be released from the reservoir in order to pass from the device and be delivered to a site in vivo to exert a therapeutic effect on a patient. However, the drug molecules may be retained within the reservoirs for certain in vitro applications.

In several embodiments, hermeticity, which is typically defined as a maximum allowable transport rate of a particular molecule (such as helium or water) for a particular application, of the sealed reservoirs is required. That is, whether a reservoir is considered hermetic can vary among different applications of the device depending upon the particular demands of the application.

Chemical Molecules

The reservoir contents can include essentially any natural or synthetic, organic or inorganic molecules or mixtures thereof. The molecules may be in essentially any form, such as a pure solid or liquid, a gel or hydrogel, a solution, an emulsion, a slurry, a lyophilized powder, or a suspension. The molecules of interest may be mixed with other materials to control or enhance the rate and/or time of release from an opened reservoir.

In a preferred embodiment, the reservoir contents comprise a drug formulation. The drug formulation is a composition that comprises a drug. As used herein, the term "drug" includes any therapeutic or prophylactic agent (e.g., an active pharmaceutical ingredient or API). In one embodiment, the drug is provided in a solid form, particularly for purposes of maintaining or extending the stability of the drug over a commercially and medically useful time, e.g., during storage in a drug delivery device until the drug needs to be administered. The solid drug matrix may be in pure form or in the form of solid particles of another material in which the drug is contained, suspended, or dispersed. In one embodiment, the drug is a protein or a peptide. Examples include glycoproteins, enzymes (e.g., proteolytic enzymes), hormones or other analogs antibodies (e.g., anti-VEGF antibodies, tumor necrosis factor inhibitors), cytokines (e.g., α-, β-, or γ-interferons), interleukins (e.g., IL-2, IL-10), and diabetes/obesity-related therapeutics (e.g., insulin, exenatide, PYY, GLP-1 and its analogs). The reservoirs in one device can include a single drug or a combination of two or more drug formulations. Different formulations can be stored together and released from the same one or more reservoirs or they can each be stored in and released from different reservoirs.

For in vitro applications, the chemical molecules can be any of a wide range of molecules where the controlled release of a small (milligram to nanogram) amount of one or more molecules is required, for example, in the fields of analytic chemistry or medical diagnostics. Molecules can be effective as pH buffering agents, diagnostic reagents, and reagents in complex reactions such as the polymerase chain reaction or other nucleic acid amplification procedures. In other embodiments, the molecules to be released are fragrances or scents, dyes or other coloring agents, sweeteners or other concentrated flavoring agents, or a variety of other compounds. In yet other embodiments, the reservoirs contain immobilized molecules. Examples include any chemical species which can be involved in a reaction, including reagents, catalysts (e.g., enzymes, metals, and zeolites), proteins (e.g., antibodies), nucleic acids, polysaccharides, cells, and polymers, as well as organic or inorganic molecules which can function as a diagnostic agent.

The drug or other molecules for release can be dispersed in a matrix material, to control the rate of release. This matrix material can be a "release system," as described in U.S. Pat. No. 5,797,898, the degradation, dissolution, or diffusion properties of which can provide a method for controlling the release rate of the chemical molecules. In one embodiment, the drug formulation within a reservoir comprises layers of drug and non-drug material. After the active release mechanism has exposed the reservoir contents, the multiple layers provide multiple pulses of drug release due to intervening layers of non-drug. Such a strategy can be used to obtain complex release profiles. See also U.S. Patent Application Publication No. 2004/0247671 A1, which is incorporated herein by reference.

Secondary Devices

As used herein, unless explicitly indicated otherwise, the term "secondary device" includes any device or a component thereof that can be located in a reservoir. In one embodiment, the secondary device is a sensor or sensing component thereof. As used herein, a "sensing component" includes a component utilized in measuring or analyzing the presence, absence, or change in a chemical or ionic species, energy, or one or more physical properties (e.g., pH, pressure) at a site. Types of sensors include biosensors, chemical sensors, physical sensors, or optical sensors. Secondary devices are further described in U.S. Pat. No. 6,551,838. In one embodiment, the sensor is a pressure sensor. See, e.g., U.S. Pat. Nos. 6,221,024, and 6,237,398, and U.S. Patent Application Publication No. 2004/0073137. Examples of sensing components include components utilized in measuring or analyzing the presence, absence, or change in a drug, chemical, or ionic species, energy (or light), or one or more physical properties (e.g., pH, pressure) at a site. In still another embodiment, the sensor includes a cantilever-type sensor, such as those used for chemical detection. For example, see U.S. Patent Application Publication No. 2005/0005676, which is incorporated herein by reference.

In a preferred embodiment, a device is provided for implantation in a patient (e.g., a human or other mammal) and the reservoir contents comprise at least one sensor indicative of a physiological condition in the patient. For example, the sensor could monitor the concentration of glucose, urea, calcium, or a hormone present in the blood, plasma, interstitial fluid, vitreous humor, or other bodily fluid of the patient.

In one embodiment, two bonded substrates include at least one cavity, which may be defined in one or both substrate portions, that contains a MEMS device. The MEMS device may be on a third substrate. The space in the sealed cavity may be evacuated or may contain an inert gas or gas mixture (e.g., nitrogen, helium). The MEMS device may be one known in the art, such as a pressure sensor, an accelerometer, a gyroscope, a resonator. In another embodiment, at least one of the bonded substrates is formed of a glass, and the cavity contains an optical sensor or chemical compound that can be optically interrogated.

Several options exist for receiving and analyzing data obtained with secondary devices located within the primary device, which can be a microchip device or another device. The primary devices may be controlled by local microprocessors or remote control. Biosensor information may provide input to the controller to determine the time and type of activation automatically, with human intervention, or a combination thereof. For example, the operation of the device can be controlled by an on-board (i.e., within the package) microprocessor or state machine. The output signal from the device, after conditioning by suitable circuitry if needed, will be acquired by the microprocessor. After analysis and processing, the output signal can be stored in a writeable computer memory chip, and/or can be sent (e.g., wirelessly) to a remote location away from the microchip. Power can be supplied to the microchip system locally by a battery or remotely by wireless transmission. See, e.g., U.S. Patent Application Publication No. 2002/0072784.

In one embodiment, a device is provided having reservoir contents that include drug molecules for release and a sensor/sensing component. For example, the sensor or sensing component can be located in a reservoir or can be attached to the device substrate. The sensor can operably communicate with the device, e.g., through a microprocessor, to control or modify the drug release variables, including dosage amount and frequency, time of release, effective rate of release, selection of drug or drug combination, and the like. The sensor or sensing component detects (or not) the species or property at the site of in vivo implantation and further may relay a signal to the microprocessor used for controlling release from the device. Such a signal could provide feedback on and/or finely control the release of a drug. In another embodiment, the device includes one or more biosensors (which may be sealed in reservoirs until needed for use) that are capable of detecting and/or measuring signals within the body of a patient. In one variation, an implantable medical device includes reservoirs comprising a sensor, sealed as described herein, and a signal from the sensor is transmitted (by any number of means, including hardwire or telemetry) to a separate drug delivery device, which could be a wearable (i.e., external) or internal pump, the signal being used in the control of the dosing of the drug.

As used herein, the term "biosensor" includes sensing devices that transduce the chemical potential of an analyte of interest into an electrical signal (e.g., by converting a mechanical or thermal energy into an electrical signal), as well as electrodes that measure electrical signals directly or indirectly. For example, the biosensor may measure intrinsic electrical signals (EKG, EEG, or other neural signals), pressure, temperature, pH, or mechanical loads on tissue structures at various in vivo locations. The electrical signal from the biosensor can then be measured, for example by a microprocessor/controller, which then can transmit the information to a remote controller, another local controller, or both. For example, the system can be used to relay or record information on the patient's vital signs or the implant environment, such as drug concentration.

In a preferred embodiment, the device contains one or more sensors for use in glucose monitoring and insulin control. Information from the sensor could be used to actively control insulin release from the same device or from a separate insulin delivery device (e.g., a conventional insulin pump, either an externally worn version or an implanted version). A hermetically sealed reservoir device may be provided in the form of an implantable multi-reservoir device storing an array of glucose sensors and capable of transmitting (by wire or wirelessly) glucose readings to a handheld or worn glucose meter-type device, which permits the patient to manually administer insulin to themselves (e.g., by injection). Other embodiments could sense other analytes and delivery other types of drugs in a similar fashion.

Reservoir Caps

As used herein, the term "reservoir cap" refers to a membrane, thin film, or other structure suitable for separating the contents of a reservoir from the environment outside of the reservoir, but which is intended to be removed or disintegrated at a selected time to open the reservoir and expose its contents. In a preferred embodiment, a discrete reservoir cap completely covers one of the reservoir's openings. In another embodiment, a discrete reservoir cap covers two or more, but less than all, of the reservoir's openings. In preferred actively controlled devices, the reservoir cap includes any material that can be disintegrated or permeabilized in response to an applied stimulus (e.g., electric field or current, magnetic field, change in pH, or by thermal, chemical, electrochemical, or mechanical means). Examples of suitable reservoir cap materials include gold, titanium, platinum, tin, silver, copper, zinc, alloys, and eutectic materials such as gold-silicon and gold-tin eutectics. Any combination of passive or active barrier layers can be present in a single device.

In one embodiment, the reservoir caps are electrically conductive and non-porous. In a preferred embodiment, the reservoir caps are in the form of a thin metal film. In another embodiment, the reservoir caps are made of multiple metal layers, such as a multi-layer/laminate structure of platinum/titanium/platinum. For example, the top and bottom layers could be selected for adhesion layers on (typically only over a portion of) the reservoir caps to ensure that the caps adhere to/bonds with both the substrate area around the reservoir openings, reservoir cap supports, and a dielectric overlayer. In one case, the structure is titanium/platinum/titanium/platinum/titanium, where the top and bottom layers serve as adhesion layers, and the platinum layers provide extra stability/biostability and protection to the main, central titanium layer. The thickness of these layers could be, for example, about 300 nm for the central titanium layer, about 40 nm for each of the platinum layers, and between about 10 and 15 nm for the adhesion titanium layers.

Control Means for Disintegrating or Permeabilizing the Reservoir Cap

The containment device includes control means that facilitates and controls reservoir opening, e.g., for disintegrating or permeabilizing the reservoir caps at a select time following sealing of the reservoirs as described herein. The control means comprises the structural component(s) and electronics (e.g., circuitry and power source) for powering and for controlling the time at which release or exposure of the reservoir contents is initiated.

The control means can take a variety of forms. In one embodiment, the reservoir cap comprises a metal film that is disintegrated by electrothermal ablation as described in U.S. Patent Application Publication No. 2004/0121486 A1, and the control means includes the hardware, electrical components, and software needed to control and deliver electric energy from a power source (e.g., battery, storage capacitor) to the selected reservoir caps for actuation, e.g., reservoir opening. For instance, the device can include a source of electric power for applying an electric current through an electrical input lead, an electrical output lead, and a reservoir cap connected therebetween in an amount effective to disintegrate the reservoir cap. Power can be supplied to the control means of the multi-cap reservoir system locally by a battery, capacitor, (bio)fuel cell, or remotely by wireless transmission, as described for example in U.S. Patent Application Publication No. 2002/0072784. A capacitor can be charged locally by an on-board battery or remotely, for example by an RF signal or ultrasound.

In one embodiment, the control means includes an input source, a microprocessor, a timer, a demultiplexer (or multiplexer). The timer and (de)multiplexer circuitry can be designed and incorporated directly onto the surface of the substrate during fabrication. In another embodiment, some of the components of the control means are provided as a separate component, which can be tethered or untethered to the reservoir portion of the device. For instance, the controller and/or power source may be physically remote from, but operably connected to and/or in communication with, the multi-cap reservoir device. In one embodiment, the operation of the multi-cap reservoir system will be controlled by an on-board (e.g., within an implantable device) microprocessor. In another embodiment, a simple state machine is used, as it typically is simpler, smaller, and/or uses less power than a microprocessor.

Other reservoir opening and release control methods are described in U.S. Pat. Nos. 5,797,898, 6,527,762, and 6,491,666, U.S. Patent Application Publication Nos. 2004/0121486, 2002/0107470 A1, 2002/0072784 A1, 2002/0138067 A1, 2002/0151776 A1, 2002/0099359 A1, 2002/0187260 A1, and 2003/0010808 A1; PCT WO 2004/022033 A2; PCT WO 2004/026281; and U.S. Pat. Nos. 5,797,898; 6,123,861; and 6,527,762, all of which are incorporated by reference herein.

Using the Multi-Cap Reservoir Systems/Devices

The multi-cap reservoir release/exposure devices and systems described herein can be used in a wide variety of applications. Preferred applications include the controlled delivery of a drug, biosensing, or a combination thereof. In a preferred embodiment, the multi-cap reservoir system is part of an implantable medical device. The implantable medical device can take a wide variety of forms and be used in a variety of therapeutic and/or diagnostic applications. In one embodiment, the reservoirs store and release a drug formulation over an extended period of time. In another embodiment, the store and contain a sensor for selective exposure, wherein the reservoirs are opened as needed (depending, for example, upon fouling of the sensor) or as dictated by a predetermined schedule. For example, the reservoirs could contain a pressure sensor, a chemical sensor, or a biological sensor. In a particular embodiment, the reservoirs comprise a glucose sensor, which may, for instance, comprise glucose oxidase immobilized on an electrode in the reservoir and coated with one or more permeable/semi-permeable membranes. Because the enzyme could lose its activity when exposed to the environment (e.g., the body) before its intended time of use, the sealed reservoir serves to protect the enzyme until it is needed.

In still other embodiments, the multi-cap reservoir systems and devices described herein are incorporated into a variety of other devices. For example, the hermetically sealed reservoirs could be integrated into other types and designs of implantable medical devices, such as the catheters and electrodes described in U.S. Patent Application Publication No. 2002/0111601. In another example, it could be incorporated into another medical device, in which the present devices and systems release drug into a carrier fluid that then flows to a desired site of administration, as illustrated for example in U.S. Pat. No. 6,491,666. The hermetically sealed reservoirs also could be incorporated into a drug pump, an inhaler or other pulmonary drug delivery device.

The sealed devices described herein also have numerous in vitro and commercial diagnostic applications. The devices are capable of delivering precisely metered quantities of molecules and thus are useful for in vitro applications, such as analytical chemistry and medical diagnostics, as well as biological applications such as the delivery of factors to cell cultures. In still other non-medical applications, the devices are used to control release of fragrances, dyes, or other useful chemicals.

Still other applications are described in U.S. Pat. Nos. 5,797,898; 6,527,762; 6,491,666; and 6,551,838, and U.S. Patent Application Publications 2002/0183721, 2003/0100865, 2002/0099359, 2004/0082937, 2004/0127942, 2004/0121486, 2004/0106914, and 2004/0106953, all of which are incorporated by reference herein.

Embodiments of the invention can further be understood with reference to the following non-limiting examples.

Example 1: Tongue and Groove Hermetic Seal

Figure 3:
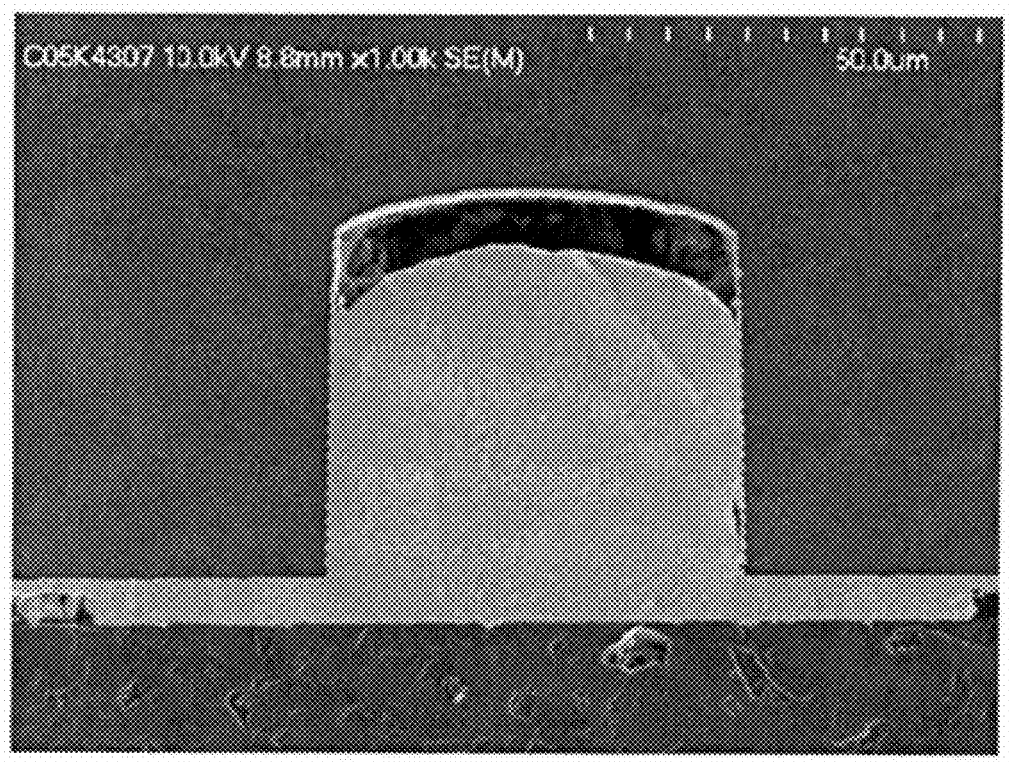
FIG. 3 is a scanning electron micrograph showing a cross-section of a hermetic seal that was made using the seal design and compression cold weld process illustrated in FIG. 2.

A hermetic seal was made using a tongue and groove joint design. The seal was made by a compression cold welding process. FIG. 3 shows an SEM of the seal. The substrates are silicon (top) and alumina (bottom). The metals are gold (sputtered on silicon, sputtered then electroplated on alumina). The parts were bonded on an FC-150 flip chip aligner, which is a machine that provides accurate alignment in x, y, z and pitch, roll, and yaw. Once the parts were aligned, the FC-150 compressed the parts together and the cold weld bond was formed.

Example 2: Variation of Feature Sizes and Metal Thickness Impact on Hermeticity Several different joint designs were fabricated, using different feature sizes and metal layer thicknesses. The joints were compression cold welded, and the sealed joints were tested for leaks using either a dye penetrant test or a He leak detector depending on the part geometry. As shown in Table 1 below, the seal integrity was found to be independent of feature size and gold metal layer thickness over the ranges tested. Undetectable leak rates may leak below the leak detectors lower limit or less than 5e-11 atm*cc/sec.

TABLE 1

Comparison of Various Joint Seals-Leak Test

| Ridge Width (188) μm | Ridge Height (190) μm | Joint structure Material | Joint Surface Metal Thickness μm | Groove Width μm | Groove Depth μm | Groove Metal Thickness μm | Overlap μm | Leak Test | Results |
|---|---|---|---|---|---|---|---|---|---|
| 145 | 50 | Gold | — | 135 | 50 | 10 | 21 | Dye penetrant | Leak Tight |
| 50 | 50 | Silicon | 7 | 80 | 50 | 7 | 2 | Dye penetrant | Leak Tight |
| 60 | 50 | Gold | — | 46 | 50 | 1 | 14 | He Leak | Undetectable |
| 60 | 50 | Gold | — | 53 | 50 | 10 | 7 | He Leak | Undetectable |
| 60 | 50 | Gold | — | 50 | 50 | 1 | 10 | He Leak | Undetectable |

Figure 27A:
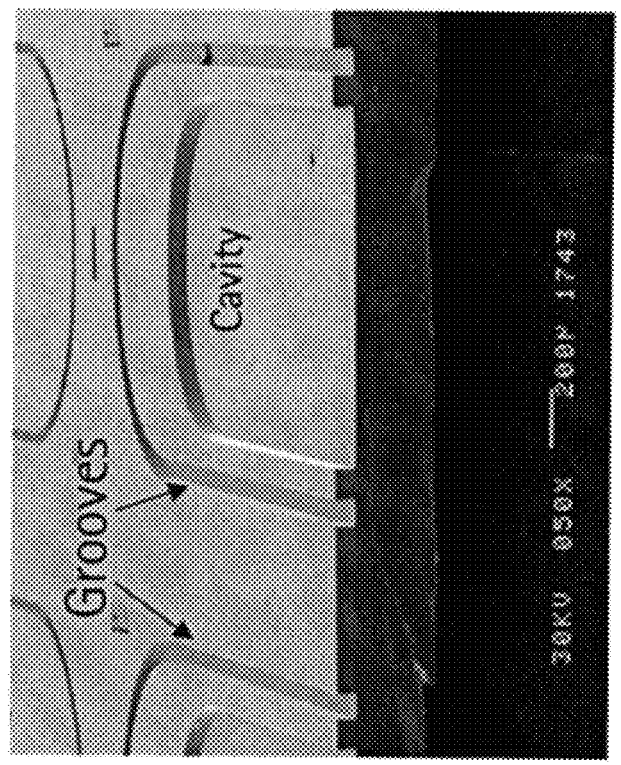
FIGS. 27A-B are scanning electron micrographs (SEMs) of two silicon substrates having microfabricated seal features for compression cold welding.
Figure 27B:
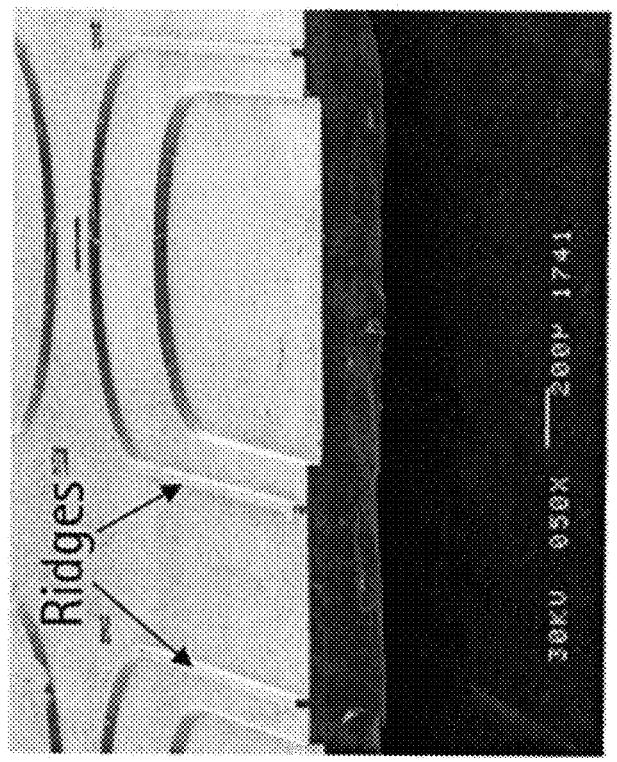

Example 3: Array of Microfabricated Cavities Having Individual Seal Features Two silicon substrates were provided made with complementary cavities and seal features for compression cold welding. The seal features included ridges that were microfabricated onto/into one substrate, and matching grooves that were microfabricated onto/into the other substrate. A shallow, wide cavity was formed inside each groove and inside each ridge. FIGS. 27A-B show the resulting substrates and seal features.

Publications cited herein are incorporated by reference. Modifications and variations of the methods and devices described herein will be obvious to those skilled in the art from the foregoing detailed description. Such modifications and variations are intended to come within the scope of the appended claims.

We claim:

1. A method of forming an electrical via connection comprising:
    providing a first non-conductive substrate having an aperture therethrough, wherein the interior surface of said first substrate defining said aperture comprises a layer of a first electrically conductive material;
    providing a second non-conductive substrate having a projecting member extending from a surface of said second substrate, wherein said projecting member is formed of or coated with a layer of a second electrically conductive material; and
    compressing the projecting member of said second substrate into the aperture of said first substrate, to locally plastically deform and shear the first and second electrically conductive materials, in an amount effective to form a cold weld and electrical connection between the first and second electrically conductive materials.

2. The method of claim 1, further comprising:
    before the step of compressing, aligning the projecting member of said second substrate relative to the aperture of said first substrate so as to impart one or more overlaps of the projecting member relative to the aperture.

3. The method of claim 2, wherein the step of compressing comprises locally deforming and shearing the projecting member at one or more interfaces created by the one or more overlaps in an amount effective to plastically deform at least a portion of the projecting member into a space between the first substrate and the second substrate outside the aperture.

4. The method of claim 1, wherein the first non-conductive substrate, the second non-conductive substrate, or both first and second non-conductive substrates comprise silicon.

5. The method of claim 4, wherein the first electrically conductive material, the second electrically conductive material, or both electrically conductive materials comprise gold, indium, aluminum, copper, lead, zinc, nickel, silver, palladium, cadmium, titanium, tungsten, tin, and combinations thereof.

6. The method of claim 2, wherein the one or more overlaps have a width of between 1 μm and 50 μm.

7. The method of claim 1, wherein the projecting member is cylindrical.

8. The method of claim 1, wherein the first non-conductive substrate is rigid.

9. The method of claim 8, wherein the first non-conductive substrate comprises silicon.

10. A method of forming an electrical via connection comprising:

providing a first non-conductive substrate having an aperture therethrough, wherein the interior surface of said first substrate defining said aperture comprises a layer of a first electrically conductive material;

providing a second non-conductive substrate having a projecting member extending from a surface of said second substrate, wherein said projecting member is formed of or coated with a layer of a second electrically conductive material; and compressing the projecting member of said second substrate into the aperture of said first substrate, to locally plastically deform and shear the first and second electrically conductive materials, in an amount effective to form a hermetic cold weld and electrical connection between the first and second electrically conductive materials.

11. The method of claim 1, wherein the first and second electrically conductive materials are gold.

12. The method of claim 10, wherein the first and second electrically conductive materials are gold.

* * * * *